(12) United States Patent
Ben-Sasson

(10) Patent No.: US 6,723,694 B1
(45) Date of Patent: *Apr. 20, 2004

(54) SHORT PEPTIDES WHICH SELECTIVELY MODULATE INTRACELLULAR SIGNALLING

(75) Inventor: Shmuel A. Ben-Sasson, Jerusalem (IL)

(73) Assignees: The Children's Medical Center Corp., Boston, MA (US); Yissum Research Development Company of the Hebrew University of Jerusalem, Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 08/861,153

(22) Filed: May 21, 1997

(51) Int. Cl.$^7$ .......................... A61K 38/00; C07K 5/00
(52) U.S. Cl. .............................. 514/2; 514/7; 530/300; 530/329
(58) Field of Search .............................. 530/300, 329; 514/2, 7

(56) References Cited

U.S. PATENT DOCUMENTS 6,174,993 B1 * 1/2001 Ben-Sasson ................ 530/326

FOREIGN PATENT DOCUMENTS

| WO | 90/01701 | * | 2/1990 |
| WO | WO 95/18823 | | 7/1995 |
| WO | WO 95/24419 | | 9/1995 |
| WO | WO 96/32411 | | 10/1996 |
| WO | WO 97/14038 | | 4/1997 |

OTHER PUBLICATIONS

CAPLUS AN 120:104302 and Ifect. Immn. 62(1) pp. 86–90, Jan. 1994.*
Songyang et al., Cell, vol. 72, pp. 767–778, 1993.*
Caplus Abstract No. 125:134514, 1996.*
Obermeier et al., J.Biol. Chem. vol. 268, No. 31 pp. 22963–22966 + Absract and RN hits, Nov. 1993.*
Kallunki et al, "JNK2 contains a specificity–determining region responsible for efficient c–Jun binding and phosphorylation", *Genes & Development* 8:2996–3007 (1994).
Taylor, S. S. et al., "cAMP–dependent protein kinase defines a family of enzymes," Phil. Trans. R. Soc. Lond. B, 340:315–324, (1993).
Mohammadi, M. et al., "Structure of the FGF Receptor Tyrosine Kinase Domain Reveals a Novel Autoinhibitory Mechanism," Cell, 86:577–587, (1996).
Hubbard, S. R. et al., "Crystal structure of the tyrosine kinase domain of the human insulin receptor," Nature, 372:22–29, (1994).
Alemà, S. et al., "Differentiation of PC12 phaeochromocytoma cells induced by v–src oncogene," Nature, 316:557–559, (1985).
Lange–Carter, C. A. et al., "A Divergence in the MAP Kinase Regulatory Network Defined by MEK Kinase and Raf," Science, 260:315–318, (1993).
Mason, I. J., "The Ins and Outs of Fibroblast Growth Factors," Cell, 78:547–552, (1994).
Hanks and Hunter, "The Eukaryotic Protein Kinase Superfamily," *IN: The Protein Kinase Facts Book, vol. I*, (Hardie et al., eds). Academic Press, Chapter 2 (1995).

* cited by examiner

*Primary Examiner*—Bennett Celsa
(74) *Attorney, Agent, or Firm*—Browdy and Neimark, P.L.L.C.

(57) ABSTRACT

Disclosed are peptides which are peptide derivatives of the HJ loop of a protein tyrosine kinase. The peptides can modulate the activity of the protein tyrosine kinase. Also disclosed are methods of modulating the activity of a protein tyrosine kinase in a subject by administering one of the peptides of the present invention.

87 Claims, 5 Drawing Sheets

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
| C-Src | T | E | L | T | T | K | G | R | V | P | Y | P | G | M | V | N | R | E | V | L |
|  | W | D | I | S | S | Y | A | K | I |  | F |  | A | R | N | K | A | D | I | M |
|  |  | E* | M | V | R |  | X | L |  |  | W |  |  | X | T |  | P | Q | L | I |
|  |  | D* | V | I | H |  |  | M |  |  |  |  |  |  | S |  | X | E* | M | V |
|  |  |  |  | L | X |  |  |  |  |  |  |  |  |  |  |  |  | D* |  |  |
|  |  |  |  | M | O |  |  |  |  |  |  |  |  |  |  |  |  |  |  |  |
| Lck | T | E | I | V | T | H | G | R | I | P | Y | P | G | M | T | N | P | E | V | I |
|  | W | D | L | I | S | K | A | K | L |  | F |  | A | R | S | K | R | D | I | L |
|  |  | E* | V | L |  | O |  | M |  |  | W |  |  |  | V |  | A | Q | L | M |
|  |  | D* |  | M |  |  |  | X |  |  |  |  |  |  |  |  |  | M |  | V |
| Csk | W | E | I | Y | S | F | G | R | V | P | Y | P | R | I | P | L | K | D | V | V |
|  |  | D | L | F | T | Y | A | K | A |  | F |  | K | M | S | I | R | E | I | I |
|  |  | E* | V | W | W |  | X |  |  |  | W |  | X | L | T | V | X | N | L | L |
|  |  | D* | M |  |  |  | O |  |  |  |  |  | O | V |  | M | O | D* | M | M |
|  |  |  |  |  |  |  |  |  |  |  |  |  |  |  |  |  |  | E* |  |  |
|  |  |  |  |  |  |  |  |  |  |  |  |  |  |  |  |  |  | Q |  |  |
| c-Abl | W | E | I | A | T | Y | G | M | S | P | Y | P | G | I | D | R | S | Q | V | Y |
|  |  | E* | L | G | S | F | A | V | T |  | F |  | A | L | E | K | T | E | I | F |
|  |  |  | V | V | W |  | V | W | L |  | W |  |  | M | D* | P |  | D | L | W |
|  |  |  |  | M |  |  |  |  | I |  |  |  |  | V | E* | L |  | N | M |  |
|  |  |  |  |  |  |  |  |  |  |  |  |  |  |  |  | I |  | E* |  |  |
|  |  |  |  |  |  |  |  |  |  |  |  |  |  |  |  | X |  | D* |  |  |
|  |  |  |  |  |  |  |  |  |  |  |  |  |  |  |  | O |  |  |  |  |
| c-Met | W | E | L | M | T | R | G | A | P | P | Y | P | D | V | N | T | F | D | I | T |
|  |  | D | I | L | S | K | A | G | S |  | F |  | E | I | D | P | Y | E | L | S |
|  |  | E* | V | I |  | Y |  |  | T |  | W |  | D* | L | E |  | W | D* | V |  |
|  |  | D* | M | V | X |  |  |  |  |  |  |  | E* | M | Q |  |  | E* | M |  |
|  |  |  |  |  | O |  |  |  |  |  |  |  |  |  | E* |  |  |  |  |  |
|  |  |  |  |  |  |  |  |  |  |  |  |  |  |  | D* |  |  |  |  |  |
| FAK | W | E | I | L | M | H | G | V | K | P | F | Q | G | V | K | N | N | D | V | I |
|  |  | D | L | I | V | K | A | A | R |  | Y | P | A | I | R | D | D | E | M | L |
|  |  | E* | M | M | L |  | G | X |  |  | W |  |  | L | X | Q | Q | D* | L | V |
|  |  | D* | V | V | I |  |  | O |  |  |  |  |  | M | O | D* | D* | E* | I | M |
|  |  |  |  |  |  |  |  |  |  |  |  |  |  |  |  | E* | E* |  |  |  |
| Lyn/Hck | Y | E | I | V | T | Y | G | K | I | P | Y | P | G | R | T | N | A | D | V | M |
|  | M | D | L | L | S | F | A | R | L |  | F |  | A | M | S | Q | P | E | L | I |
|  |  | E* | V | M |  | W |  | X | M |  | W |  |  | X |  |  | G | D* | I | L |
|  |  | D* | M | I |  |  |  | O | V |  |  |  |  |  |  |  |  | E* | M | V |

Figure 2A

```
          1  2  3  4  5  6  7  8  9 10 11 12 13 14 15 16 17 18 19 20
Endoth    W  E  I  F  S  L  G  G  T  P  Y  P  G  M  M  V  D  E  T  F
          D  L  V  T  I  A  A  S     F  C  A  L  T  M  N  S  L  Y
          E* M  W     M              W  A     V  P  C  A  T  Q  W
          D* V        V                 S     I  Q  I     E* D
                                              K  L        D  E
                                              S  S        D* N
                                              O              E*
                                                             D*

Trk-      W  E  I  F  T  Y  G  K  Q  P  W  Y  Q  L  S  N  T  E  A  I
NGFR      D  V  W  S  W  A  O  N     Y  F  N  I  T  Q  N  D  V  L
          E* M  Y  F                 F  W     W           E* G  V
          D* L                                M           D*    M

RET       W  E  I  V  T  L  G  G  N  P  Y  P  G  I  P  P  E  R  L  F
          D  V  I  S  V  A  A  Q     W     A  V           D  X  M  W
          E* M  M  M                 F        M           E* K  V  Y
          D* L  L  I                          L           D* O  I 1  2  3  4  5  6  7  8  9 10 11 12 13 14 15 16 17 18 19 20
```

D* = a substituted or unsubstituted aliphatic, benzylic or aromatic ester of aspartic acid E* = a substituted or unsubstituted aliphatic, benzylic or aromatic ester of glutamic acid X = N-nitroarginine, β-cycloarginine, γ-hydroxyarginine, amidinocitroline or 2-amino-4-guanidinobutanoic acid O = ornithine

Figure 2B

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|

C-Src

| Name | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| HJ4 |  |  | Ac- | L | V | T | K |  | G | R | V | -NH2 |  |  |  |  |  |  |  |  |
| HJ20 |  |  | Ac- | L | T | T | K |  | G | R | V | -NH2 |  |  |  |  |  |  |  |  |
| HJ20.1 |  |  | NH2- | L | T | T | K |  | G | R | V | -NH2 |  |  |  |  |  |  |  |  |
| HJ4.2 |  |  | Ac- | L | V | T | K |  | G | R | V | -COOH |  |  |  |  |  |  |  |  |
| HJ18 |  |  |  | Ac- | V | T | K |  | G | R | V | -NH2 |  |  |  |  |  |  |  |  |
| HJ4 Nitro |  |  | Ac- | L | V | T | K |  | G | R^V | -NH2 |  |  |  |  |  |  |  |  |  |
| HJ12 |  |  | Ac- | L | V | T | K* |  | G | R | V | -NH2 |  |  |  |  |  |  |  |  |
| HJ40 |  |  | Ac- | V | V | T | R |  | G | K | V | -NH2 |  |  |  |  |  |  |  |  |
| J49 |  |  | Ac- | L | V | T | K |  | K*R | V | -NH2 |  |  |  |  |  |  |  |  |  |
| HJ11 |  |  |  |  | Ac- | G | R | V | P |  | F | P | G | -NH2 |  |  |  |  |  |  |
| HJ21.1 |  |  |  |  | NH2- | G | R | V | P |  | Y | P | G | -NH2 |  |  |  |  |  |  |
| HJ11.1 |  |  |  |  | NH2- | G | R | V | P |  | F | P | G | -NH2 |  |  |  |  |  |  |
| HJ22 |  |  |  | Ac2- | K | G | R | V | P |  | Y | P | G | -NH2 |  |  |  |  |  |  |
| HJ11 Met |  |  |  |  | Ac- | G | R | M | P |  | Y | P | G | -NH2 |  |  |  |  |  |  |
| HJ30 |  |  |  |  | Ac- | G | R^VP |  |  |  | Y | P | G | M |  | V | -NH2 |  |  |  |
| HJ6 | Ac- | E |  | L | V | T | K |  | G | R | V | P |  | Y | -NH2 |  |  |  |  |  |
| HJ8 |  |  | Ac- | L | V | T | K |  | G | R | V | P |  | F | P | G | -NH2 |  |  |  |
| Lena1 | Ac- | E" |  | L | V | T | K |  | G | R | V | P |  | Y | P | G | -NH2 |  |  |  |
| Lena2 |  | E |  | L | V | T | K |  | G | R | V | P |  | Y | P | G | -NH2 |  |  |  |

Lyn/Hck

| Name | 1 | 2 | 3 | 4 | 5 | 6 | 7 | 8 | 9 | 10 | 11 |
|---|---|---|---|---|---|---|---|---|---|---|---|
| HJ24 |  |  | Ac- | I | V | T | Y |  | G | K | I | -NH2 |
| HJ32 |  |  | Ac- | I | V | T | Y |  | G | R | I | -NH2 |

Figure 3A

|  |  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|

Lck

| HJ13 | Ac- | L | V | T | H |  |  | G | R | V |  |  |  |  |  |  |  |  | -NH2 |  |  |
|---|---|---|---|---|---|---|---|---|---|---|---|---|---|---|---|---|---|---|---|---|---|
| HJ23.1 | Ac- | I | V | T | H |  |  | G | R | I |  |  |  |  |  |  |  |  | -NH2 |  |  |

Csk

| HJ27 | Ac- | I | Y | S | F |  |  | G | R | V |  |  |  |  |  |  |  |  | -NH2 |  |  |
|---|---|---|---|---|---|---|---|---|---|---|---|---|---|---|---|---|---|---|---|---|---|
| HJ31 |  |  |  |  | Ac- | G | R | V | P |  |  | Y | P | R | I |  |  | P | L | K | -NH2 | c-Abl

| HJ25 | Ac- | I | A | T | Y |  |  | G | M | S |  |  |  |  |  |  |  |  | -NH2 |  |  |
|---|---|---|---|---|---|---|---|---|---|---|---|---|---|---|---|---|---|---|---|---|---|
| HJ33 |  |  |  |  |  | Ac- | Y |  |  | G | M | S | P |  |  | Y | P | G | I | -NH2 |  |

C-Met

| HJ28 | Ac- | L | M | T | R |  |  | G | A | P |  |  |  |  |  |  |  |  | -NH2 |  |  |
|---|---|---|---|---|---|---|---|---|---|---|---|---|---|---|---|---|---|---|---|---|---|
| HJ29 |  |  |  |  | Ac- | G | A | P | P |  |  | Y | P | D! |  |  |  |  | -NH2 |  |  |

FAK

| HJ34 |  |  |  |  | Ac- | G | V | K | P |  |  | F | Q | G | V |  |  | K | N | N | -NH2 |
|---|---|---|---|---|---|---|---|---|---|---|---|---|---|---|---|---|---|---|---|---|---|

Endothelial

| HJ7 | Ac- | I | F | S | L |  |  | G | G | S |  |  |  |  |  |  |  |  | -NH2 |  |  |
|---|---|---|---|---|---|---|---|---|---|---|---|---|---|---|---|---|---|---|---|---|---|
| HJ7.1 | NH2- | I | F | S | L |  |  | G | G | S |  |  |  |  |  |  |  |  | -NH2 |  |  |
| HJ15 |  |  |  |  | Ac- | G | G | S | P |  |  | Y | P | G |  |  |  |  | -NH2 |  |  |
| HJ9 | Ac- | I | F | S | L |  |  | G | G | S | P |  |  | F | P | G |  |  | -NH2 |  |  |

Trk-NGFR

| HJ10 | Ac- | I | F | T | Y |  |  | G | K | Q |  |  |  |  |  |  |  |  | -NH2 |  |  |
|---|---|---|---|---|---|---|---|---|---|---|---|---|---|---|---|---|---|---|---|---|---|
| HJ14 |  |  |  |  | Ac- | G | K | Q | P |  |  | W | Y | Q |  |  |  |  | -NH2 |  |  |

K* - D-Lysine
R^ - N-Nitroarginine
E! - Benzylic Ester of Glutamic Acid
E" - Methyl Ester of Glutamic Acid
D! - Benzylic Ester of Aspartic Acid

SHORT PEPTIDES WHICH SELECTIVELY MODULATE INTRACELLULAR SIGNALLING

BACKGROUND OF THE INVENTION

Protein tyrosine kinases are a member of the eukaryotic protein kinase superfamily. Enzymes of this class specifically phosphorylate tyrosine residues of intracellular proteins and are important in mediating signal transduction in multicellular organisms. Protein tyrosine kinases occur as membrane-bound receptors, which participate in transmembrane signaling, or as intracellular proteins which take part in signal transduction within the cell, including signal transduction to the nucleus.

As such, phosphorylation of tyrosine by protein tyrosine kinases is an important mechanism for regulating intracellular events in response to environmental changes. A wide variety of cellular events, including cytokine responses, antigen-dependent immune responses, cellular transformation by RNA viruses, oncogenesis, regulation of the cell cycle and modification of cell morphology and phenotype are regulated by protein tyrosine kinases. Enhanced protein tyrosine kinase activity can lead to persistent stimulation by secreted growth factors which, in turn, can lead to proliferative diseases such as cancer, to nonmalignant proliferative disease such as arteriosclerosis, psoriasis and to inflammatory response such as septic shock. Decreased function can also be lead to disease. For example, a decrease in the activity of insulin receptor tyrosine kinase is a cause of various types of diabetes and severe reduction of the B cell progenitor kinase leads to human X-linked agammaglobulinemia.

Thus, there is a need for compounds which can modulate the expression of protein tyrosine kinases. Such compounds have utility in the treatment of diseases caused by over activity or underactivity of protein tyrosine kinases. Such compounds also have utility in studying the mode of action of protein tyrosine kinases and how these proteins regulate cellular functions and activities.

SUMMARY OF THE INVENTION

It has now been found that short peptides which are derivatives of the HJ loop of a number of different protein tyrosine kinases can significantly affect the activities of cells expressing the protein tyrosine kinase. "HJ loop" is defined hereinbelow. A number of examples are listed below:

Peptide derivatives of the HJ loop of c-Src Csk, c-Abl and c-Met have been found to inhibit the proliferation of a number of a different endothelial cell types (Examples 2 and 4).

Yet other peptide derivatives of the HJ loop of c-Src, Lck and endothelial cells' tyrosine kinase receptors (Endoth) have been found to stimulate the proliferation of bovine capillary endothelial cells in vi tro (Example 2).

Peptide derivatives of the HJ loop of Lyn/Hck have been found to cause morphological changes in vascular smooth muscle cells in vitro (Example 5).

Specifically, cells incubated with Ac-IVTYGKI-NH$_2$ (SEQ ID NO.: 1) and Ac-IVTYGRI-NH$_2$ (SEQ ID NO.: 2), referred to as HJ24 and HJ32, respectively, become elongated and assume a spindle-like structure.

Peptide derivatives of the HJ loop of c-Src have been found to protect PC-12 neuronal cells in vitro from the effects of serum deprivation (Example 3).

Based on the aforementioned discoveries, novel peptides are disclosed herein which are peptide derivatives of the HJ loop of protein tyrosine kinases. Also disclosed are methods of identifying a peptide derivative of an HJ loop of a protein tyrosine kinase which modulates the activity of said protein tyrosine kinase. Methods of modulating the activity of a protein tyrosine kinase in a subject are also disclosed.

One embodiment of the present invention is a novel peptide which is a peptide derivative of the HJ loop of a protein tyrosine kinase. The peptide comprises between about five and about twenty amino acid residues or amino acid residue analogs and modulates the activity of the protein tyrosine kinase. The N-terminus and/or C-terminus of the peptide can be substituted or unsubstituted. The peptide can be linear or cyclic.

Another embodiment of the present invention is a method of modulating the activity of a protein tyrosine kinase in a subject. The method comprises administering a therapeutically effective amount of a peptide which is a derivative of an HJ loop of said protein tyrosine kinase, as described above.

Yet another embodiment of the present invention is a method of identifying a peptide which modulates the activity of a protein tyrosine kinase. The method comprises providing a "test peptide" which has from about five to about twenty amino acids or amino acid analogs and which is a peptide derivative of the HJ loop of said protein tyrosine kinase. The test peptide is incubated with cells having a cellular activity or function under the control of said protein tyrosine kinase under conditions suitable for assessing the activity of the protein tyrosine kinase. The activity of the protein tyrosine kinase is assessed and compared with cells of the same cell type grown under the same conditions in the absence of the test peptide. A greater or lesser activity compared with cells grown in the absence of the test peptide indicates that the test peptide modulates activity of the protein tyrosine kinase.

The peptides of the present invention can be used in the treatment of a wide variety of diseases caused by overactivity and underactivity of a protein tyrosine kinase. Examples include, but are not limited to, cancer, diseases caused by proliferation of smooth muscle (e.g., restinosis and atherosclerosis) psoriasis, inflammatory disorders, diabetes, immune disorders and osteoporosis. The peptides of the present invention also have in vitro utilities, for example, in the generation of antibodies which specifically bind the protein tyrosine kinase whose HJ loop has a sequence or subsequence corresponding to the peptide. These antibodies can be used to identify cells expressing the protein tyrosine kinase and to study the intracellular distribution of the protein tyrosine kinase. In addition, the peptides can be used to identity and quantitate ligands which bind the HJ loop of the protein tyrosine kinase from which the peptide was derived.

BRIEF DESCRIPTION OF THE FIGURES

FIG. 1 is a sequence illustrating the consensus sequence (SEQ ID NO.: 49) of the HJ loop found among the family of protein tyrosine kinases.

FIGS. 2A–2B are a Table illustrating the amino acid sequence of the HJ loop of the protein tyrosine kinases c-Src (SEQ ID NO.: 3), Lck (SEQ ID NO.: 4), Csk (SEQ ID NO.: 5), c-Abl (SEQ ID NO.: 6), c-Met (SEQ ID NO.: 7), FAK (SEQ ID NO.: 8), Lyn/Hck (SEQ ID NO.: 9), Endoth (SEQ ID NO.: 10), Trk-nerve growth factor (Trk-NGFR) (SEQ ID NO.: 11), and RET (SEQ ID NO.: 12). Also shown are examples of suitable conservative substitutions in these amino acid sequences. The variations for RET are set forth in SEQ ID NO.: 50. A "*" indicates that the carboxylic acid group in the side chain of the amino acid is protected as an aliphatic, substituted aliphatic, benzylic, substituted benzylic, aromatic or substituted aromatic ester.

FIGS. 3A–3B are a Table illustrating the sequences of the peptides HJ4 (SEQ ID NO.: 13), HJ4.2 (SEQ ID NO.: 14), HJ4Nitro (SEQ ID NO.: 15), HJ6 (SEQ ID NO.: 16), HJ7 (SEQ ID NO.: 17), HJ7.1 (SEQ ID NO.: 18), HJ8 (SEQ ID NO.: 19), HJ9 (SEQ ID NO.: 20), HJ10 (SEQ ID NO.: 21), HJ11 (SEQ ID NO.: 22), HJ1.1 (SEQ ID NO.: 23), HJ11Met (SEQ ID NO.: 24), HJ12 (SEQ ID NO.: 25), HJ13 (SEQ ID NO.: 26), HJ14 (SEQ ID NO.: 27), HJ15 (SEQ ID NO.: 28), HJ18 (SEQ ID NO.: 29), HJ20, (SEQ ID NO.: 30), HJ20.1 (SEQ ID NO.: 31), HJ21.1 (SEQ ID NO.: 32), HJ22 (SEQ ID NO.: 33), HJ23.1 (SEQ ID NO.: 34), HJ24 (SEQ ID NO.: 1), HJ25 (SEQ ID NO.: 35), HJ27 (SEQ ID NO.: 36), HJ28 (SEQ ID NO.: 37), HJ29 (SEQ ID NO.: 48), HJ30 (SEQ ID NO.: 38), HJ31 (SEQ ID NO.: 39), HJ32 (SEQ ID NO.: 2), HJ33 (SEQ ID NO.: 40), HJ34 (SEQ ID NO.: 41), HJ40 (SEQ ID NO.: 47), Lena 1 (SEQ ID NO.: 42), Lena 2 (SEQ ID NO.: 43) and J49 (SEQ ID NO.: 44). FIGS. 3A–3B also indicate from which protein tyrosine kinase each peptide is derived and to which portion of the HJ loop the sequence of each peptide corresponds.

DETAILED DESCRIPTION OF THE INVENTION

A protein tyrosine kinase (hereinafter "PTK") is a membrane bound or intracellular protein which uses the gamma phosphate of ATP or GTP to generate phosphate monoesters on the phenolic group of a tyrosine residue. PTKs have homologous "kinase domains" or "catalytic domains" which carry out this phosphorylation. Based on a comparison of a large number of protein kinases, it is now known that the kinase domain of protein kinases, including PTKs, can be divided into twelve subdomains, which are regions generally uninterrupted by large amino acid insertions and contain characteristic patterns of conserved residues (Hanks and Hunter, "The Eukaryotic Protein Kinase Superfamily", in Hardie and Hanks (ed.), *The Protein Kinase Facts Book, Volume I*, Academic Press, Chapter 2, 1995). These subdomains are referred to as Subdomain I through Subdomain XII.

The "HJ loop" referred to herein is found within the kinase domain of PTKs between the middle of Subdomain IX and the middle of Subdomain X. Because of the high degree of homology found in the subdomains of different protein kinases, including PTKs, the amino acid sequences of the domains of different PTKs can be aligned. Thus, the HJ loop of a PTK can be defined by reference to the amino acid sequence of a prototypical protein kinase, for example PKA-Cα, and can be said to correspond to a contiguous sequence of about twenty amino acid residues found between about amino acid 229 and 248 of PKA-Cα.

A second definition of the HJ loop of a PTK, which is complementary to the definition provided in the preceding paragraph, can be made by reference to the three dimensional structure of the kinase domain of PTKs. The kinase domain of PTKs has been found to contain at least nine alpha helices, referred to as helix A through helix I (Taylor et al., *Phil. Trans. R. Soc. Lond. B*340:315 (1993), Mohammadi et al., *Cell* 86:577 (1996) and Hubbard et al., *Nature* 372:746 (1994)). The HJ loop is a contiguous sequence of about twenty amino acids beginning within the F helix about five amino acids residues from the N-terminus of the F helix and extending about five amino acid residues into the G helix.

Optionally, the C-terminus or the N-terminus of the peptides of the present invention, or both, can be substituted with a carboxylic acid protecting group or an amine protecting group, respectively. Suitable protecting groups are described in Green and Wuts, "*Protecting Groups in Organic Synthesis*", John Wiley and Sons, Chapters 5 and 7, 1991, the teachings of which are incorporated herein by reference. Preferred protecting groups are those which facilitate transport of the peptide into a cell, for example, by reducing the hydrophilicity and increasing the lipophilicity of the peptide. Examples of N-terminal protecting groups include acyl groups (—CO—$R_1$) and alkoxy carbonyl or aryloxy carbonyl groups (—CO—O—$R_1$), wherein R, is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, phenyl-CO—, substituted phenyl-CO—, benzyl-CO— and (substituted benzyl)-CO—. Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. The carboxyl group at the C-terminus can be protected, for example, as an amide (i.e., the hydroxyl group at the C-terminus is replaced with —$NH_2$, —$NHR_2$ and —$NR_2R_3$) or ester (i.e., the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0–2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl) (ethyl), —NH(benzyl), —N(C1–C4 alkyl) (benzyl), —NH (phenyl), —N (C1–C4 alkyl) (phenyl), —$OCH_3$, —O-(ethyl), —O-(n-propyl), —O-(n-butyl), —O-(iso-propyl), -O-(sec-butyl), —O-(t-butyl), —O-benzyl and —O-phenyl.

A "peptide derivative of the HJ loop" includes a peptide having the amino acid sequence of the HJ loop. A "peptide derivative of the HJ loop" also includes, for example, a subsequence of the HJ loop of the PTK. A subsequence is a contiguous sequence of from about five to about twenty amino acids found within a larger sequence. Thus, a subsequence of the HJ loop is a contiguous sequence of from about five to about twenty amino acids found within the HJ loop. A subsequence of the HJ loop can also be referred to as a "fragment" of the HJ loop.

A "peptide derivative" also includes a peptide having a "modified sequence" in which one or more amino acids in the original sequence or subsequence have been substituted with a naturally occurring amino acid or amino acid analog (also referred to as a "modified amino acid"). In one aspect of the present invention, the peptide derivative has a sequence corresponding to a subsequence of the HJ loop of a PTK, with the proviso that any one amino acid residues in the peptide derivative can differ from the corresponding amino acid residue in the subsequence. For example, if the subsequence is [$AA_1$]-[$AA_2$]-[$AA_3$]-[$AA_4$]-[$AA_5$], then the peptide derivative can be [$AA_1$']-[$AA_2$]-[$AA_3$]-[$AA_4$]-[$AA_5$], [$AA_1$]-[$AA_2$']-[$AA_3$]-[$AA_4$]-[$AA_5$], [$AA_1$]-[$AA_2$]-[$AA_3$']-[$AA_4$]-[$AA_5$], [$AA_1$]-[$AA_2$]-[$AA_3$]-[$AA_4$']-[$AA_5$]

and [AA$_1$]-[AA$_2$]-[AA$_3$]-[AA$_4$]-[AA$_5$'], wherein [AA'] is a naturally occurring or modified amino acid different from [AA]. In another aspect of the present invention, the peptide derivative has a sequence corresponding to a subsequence of the HJ loop of a PTK, with the proviso that any two amino acid residues in the peptide derivative can differ from the corresponding amino acid residue in the subsequence.

An "amino acid residue" is a moiety found within a peptide and is represented by —NH—CHR—CO—, wherein R is the side chain of a naturally occurring amino acid. When referring to a moiety found within a peptide, the terms "amino acid residue" and "amino acid" are used interchangeably in this application. An "amino acid residue analog" includes D or L residues having following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. When referring to a moiety found within a peptide, the terms "amino acid residue analog" and "amino acid analog" are used interchangeably in this application.

As used herein, aliphatic groups include straight chained, branched or cyclic C1–C6 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include, for example, —OH, halogen (—Br, —Cl, —I and —F) —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C (=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have more than one substituent.

Suitable substitutions for amino acid residues in the sequence of an HJ loop or a subsequence of an HJ loop include conservative substitutions which result in peptide derivatives which modulate the activity of a PTK. A conservative substitution is a substitution in which the substituting amino acid (naturally occurring or modified) has about the same size and electronic properties as the amino acid being substituted. Thus, the substituting amino acid would have the same or a similar functional group in the side chain as the original amino acid.

A "conservative substitution" also refers to utilizing a substituting amino acid which is identical to the amino acid being substituted except that a functional group in the side chain is functionalized with a suitable protecting group. Suitable protecting groups are described in Green and Wuts, "Protecting Groups in Organic Synthesis", John Wiley and Sons, Chapters 5 and 7, 1991, the teachings of which are incorporated herein by reference. As with N-terminal and C-terminal protecting group, preferred protecting groups are those which facilitate transport of the peptide into a cell, for example, by reducing the hydrophilicity and increasing the lipophilicity of the peptide, and which can be cleaved, either by hydrolysis or enzymatically, inside the cell (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); Tunek et al., Biochem. Pharm. 37:3867 (1988), Anderson et al., Arch. Biochem. Biophys. 239: 538 (1985) and Singhal et al., FASEB J. 1:220 (1987)). Suitable hydroxyl protecting groups include ester, carbonate and carbamate protecting groups. Suitable amine protecting groups include acyl groups and alkoxy or aryloxy carbonyl groups, as described above for N-terminal protecting groups. Suitable carboxylic acid protecting groups include aliphatic, benzyl and aryl esters esters, as described above for C-terminal protecting groups. In one embodiment, the carboxylic acid group in the side chain of one or more glutamic acid or aspartic acid residues in a peptide of the present invention is protected, preferably as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine, serine, cysteine, threonine and modified amino acids having the following side chains: ethyl, n-butyl, —CH$_2$CH$_2$OH, —CH$_2$CH$_2$CH$_2$OH, —CH$_2$CHOHCH$_3$ and —CH$_2$SCH$_3$. Preferably, Group I includes leucine, isoleucine, valine and methionine.

Group II includes glycine, alanine, valine, serine, cysteine, threonine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, —NH$_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamate, asparagine, CO—NH-alkylated glutamate or asparagine (e.g., methyl, ethyl, n-propyl and iso-propyl) and modified amino acids having the side chain —(CH$_2$)$_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate.

Group V includes histidine, lysine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional methylene units in the side chain.

Group VI includes serine, threonine, cysteine and modified amino acids having C1–C5 straight or branched alkyl side chains substituted with —OH or —SH. Preferably, Group VI includes serine, cysteine or threonine.

Figure 1:
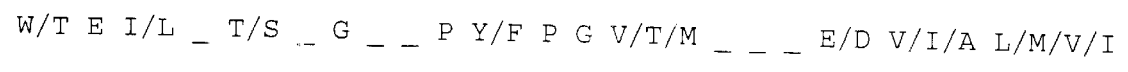

In another aspect, suitable substitutions for amino acid residues in the sequence of an HJ loop or a subsequence of an HJ loop include "severe" substitutions which result in peptide derivatives which modulate the activity of a PTK. Severe substitutions which result in peptide derivatives that modulate the activity of a PTK are much more likely to be possible in positions which are not highly conserved throughout the family of protein tyrosine kinases than at positions which are highly conserved. FIG. 1 shows the consensus sequence of the about 20 amino acids of HJ loop. Positions which are highly conserved among the PTK family and the conserved amino acids generally found in those positions have been indicated. Positions which are not as highly conserved among the PTK family of proteins have been left blank.

A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cycohexylmethyl glycine for alanine, isoleucine for glycine, a D amino acid for the corresponding L amino acid or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —(CH$_2$)$_4$COOH for the side chain of serine. These examples are not meant to be limiting.

Another example of a suitable severe substitution is the replacement of conserved glycine residues (e.g., positions seven and thirteen in FIG. 1) with D-configuration amino acids or analogs thereof, which have a hydrogen atom at a position identical to the glycine hydrogen side-chain. J49 is an example of a peptide with such a severe substitution (D-lysine for conserved glycine).

Examples of PTKs whose activity can be modulated by peptide and peptide derivatives, as described herein, include, but are not limited to, PTKs belonging to the following PTK families: Src, EGF-R, FGF-R, VEGF-R, HGF-R, PDGF-R, the insulin receptor family and the neurotrophin receptor family. Suitable members of the Src family include, but are not limited to, c-Src, c-Yes, FYN, FGR, HCK, LYN, LCK and BLK. Suitable members of the EGF-R family include, but are not limited to EGFR, ErbB2, ErbB3 and ErbB4. Suitable members of the FGF-R family include, but are not limited to FGFR1, FGFR2, FGFR3 and FGFR4. Suitable members of the VEGF-R family include, but are not limited to, Flt1, Flt4 and Flk1. Suitable members of the insulin receptor family include, but are not limited to, INS-R, IRR and IGF1-R. Other suitable PTKs include, but are not limited to, RET, CSK, c-Met, c-Abl and FAK.

The present invention includes peptides having amino acid sequences corresponding to the sequence found in the HJ loop of PTKs, subsequences thereof and modified subsequences thereof. Examples of suitable subsequences include, but are not limited to, sequences corresponding to $[AA]_1$ through $[AA]_{20}$, $[AA]_3$ through $[AA]_{10}$, $[AA]_7$ through $[AA]_{14}$, $[AA]_{11}$ through $[AA]_{18}$, $[AA]_3$ through $[AA]_{14}$, $[AA]_7$ through $[AA]_{18}$ and $[AA]_3$ through $[AA]_{18}$ of the HJ loop of a PTK, and subsequences thereof. FIGS. 2A–2B show the sequences of the HJ loop of the following PTKs: c-Src, Lck, Csk, c-Abl, c-Met, FAK, Lyn/Hck, Endoth and Trk-NGFR.

FIGS. 2A–2B also provide a numbering scheme for the amino acid sequence in an HJ loop. The amino acid at the N-terminus of the HJ loop is at position 1 and can be referred to as "$[AA]_1$". The next amino acid in the sequence, referred to as "$[AA]_2$", is at position 2 and is followed by amino acids $[AA]_3$ through $[AA]_{20}$, which are at positions 3–20. Thus, a peptide 20-mer with an amino acid sequence $[AA]_1$ through $[AA]_{20}$ includes the twenty amino acids in the HJ loop. A peptide derivative of the HJ loop with an amino acid sequence $[AA]_3$ through $[AA]_1$, as recited in the preceeding paragraph, includes the third amino acid through the tenth amino acid in said HJ loop.

The present invention also includes peptides having amino acids sequences corresponding to a modified sequence or subsequence of the HJ loop of PTKs and which modulate the activity of PTKs. In one aspect, one, two or more of the amino acids in the sequence or subsequence are modified with conservative substitutions; the substitutions can be in consensus positions, in non-consensus positions or in both. FIGS. 2A–2B also provide examples of suitable conservative amino acid substitutions for the HJ loop of c-Src, Lyn/Hck, Lck, Csk, c-Abl, c-Met, FAK, Endoth and nerve growth factor (Trk-NGFR). In another aspect, one, two or more of the amino acids in the sequence or subsequence are modified with severe substitutions; the substitutions are preferably in non-consensus positions.

Specific examples of peptide derivatives of the present invention include peptides shown in FIGS. 3A–3B. The N-terminus and/or C-terminus of these peptides can be modified, as described above. As indicated in FIGS. 3A–3B, the N-terminal of these peptides is typically acetylated and the C-terminal is typically amidated. Other protecting groups for amides and carboxylic can be used, as described above. Optionally, one or both protecting groups can be omitted. The peptides may by cyclic or linear.

Also included are peptides shown in FIGS. 3A–3B with the proviso that any one of the amino residues in the peptide can vary, being any naturally occurring amino acid or analog thereof. The present invention also includes the peptides shown in FIGS. 3A–3B with the proviso that any two of the amino residues in the peptide can vary, being any naturally occurring amino acid or analog thereof.

Other specific examples of a peptide included within the present invention is a peptide having the sequence Leu-Val- Thr-Xaa-Gly-Arg-Val (SEQ ID NO.: 45) or Gly-Arg-Val-Pro-Yaa-Pro-Zaa (SEQ ID NO.: 46). The N-terminus and/or the C-terminus can optionally be protected, for example, N-acetylated and/or C-amidated. Xaa is selected from the group consisting of L-lysine, D-lysine, histidine, tyrosine, phenylalanine and arginine; Yaa is selected from the group consisting of tyrosine, phenylalanine and tryptophan; Zaa is selected from the group consisting of glycine, alanine and arginine.

The present invention also includes cyclic peptides having amino acids sequences corresponding to a modified sequence or subsequence of the HJ loop of PTKs and which modulate the activity of PTKs.

A "cyclic peptide". refers, for example, to a peptide or a peptide or peptide derivative in which a ring is formed by a peptide bond between the nitrogen atom at the N-terminus and the carbonyl carbon at the C-terminus.

"Cyclized" also refers to forming a ring by a covalent bond between the nitrogen at the N-terminus of the compound and the side chain of a suitable amino acid in the peptide, preferably the C-terminal amino acid. For example, an amide can be formed between the nitrogen atom at the N-terminus and the carbonyl carbon in the side chain of aspartic acid or glutamic acid. Alternatively, the peptide or peptide derivative can be cyclized by forming a covalent bond between the carbonyl at the C-terminus of the compound and the side chain of a suitable amino acid in the peptide, preferably the N-terminal amino acid. For example, an amide can be formed between the carbonyl carbon at the C-terminus and the amino nitrogen atom in the side chain of lysine or ornithine; an ester can be formed between the carbonyl carbon at the C-terminus and the hydroxyl oxygen atom in the side chain of serine or threonine.

"Cyclized" also refers to forming a ring by a covalent bond between the side chains of two suitable amino acids in the peptide, preferably the terminal amino acids. For example, a disulfide can be formed between the sulfur atoms in the side chains of two cysteines. Alternatively, an ester can be formed between the carbonyl carbon in the side chain of, for example, glutamic acid or aspartic acid, and the oxygen atom in the side chain of, for example, serine or threonine. An amide can be formed between the carbonyl carbon in the side chain of, for example, glutamic acid or aspartic acid, and the amino nitrogen in side chain of, for example, lysine or ornithine.

In addition, a peptide or peptide derivative can be cyclized with a linking group between the two termini, between one terminus and the side chain of an amino acid in the peptide or peptide derivative, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

Suitable substitutions in the original amino acid sequence or subsequence are those which result in a peptide derivative, as defined above, which modulates the activity of a PTK. The activity of a PTK is "modulated" when the activity of the PTK is increased or decreased. An increase or decrease in the activity of a PTK can be detected by a corresponding modulation, increase or decrease, in a cellular activity or function which is under the control of the PTK. Examples of these cellular functions include cell proliferation, cell differentiation, cell morphology or gene expression.

It can be readily determined whether a peptide or peptide derivative modulates the activity of a PTK by obtaining cells which have one or more cellular activities controlled by a PTK. The cells are incubated with the peptide or peptide derivative to produce a test mixture under conditions suitable for assessing activity of the protein tyrosine kinase. The activity of the PTK is assessed and compared with a suitable control, e.g., the activity of the same cells incubated under the same conditions in the absence of the peptide or peptide derivative. A greater or lesser activity of the PTK in the test mixture compared with the control indicates that the test peptide or peptide derivative modulates the activity of said PTK.

Suitable cells for the assay include normal cells which express a membrane bound or intracellular PTK, transformed cells or cells which have been genetically engineered to express a PTK. Other suitable cells include cancer cells, which can be assayed for proliferation and differentiation; for example, Src, Csk and Fak are related to a whole spectrum of malignant cells. In addition, specific tumors with their corresponding involved Ptks can be used, including breast and ovarian cancer cells (EGFR), prostrate cancer cells (FGF), leukemia cells (Abl) hepatoma cells (Met). Vascular smooth muscle cells can be assayed for proliferation and migration (FGFRs and PDGFRs). Cells of the immune system can be assayed for cytokine production such as IL-2, TNF and INF (Lyn, Hck, Blk and Lck). Osteoclasts can be assayed for bone resorption (Src and Csk). Neuronal cells can be assayed for differentiation (Trks). Epithelial tissues such as epidermis, intestinal epithelium and breast can be assayed for proliferation, differentiation and regeneration (EGFRs). Liver cells can be assayed for proliferation, differentiation and regeneration (c-Met). Endothelial cells can be assayed for proliferation and migration (VEGFRs, FGFRs and c-Met).

Conditions suitable for assessing PTK activity include conditions suitable for assessing activity of a cellular activity or function under control of the PTK. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors, etc.). Conditions suitable for cell growth are used when the cellular activity or function being assessed is, for example, cell proliferation, differentiation, cell morphology, gene expression, cell survival, cell response to external stimuli and cell phenotype.

In another aspect, the activity of a PTK can be evaluated by growing the cells under serum deprivation conditions. Cells are typically grown in culture in the presence of a serum such as bovine serum, horse serum or fetal calf serum. Many cells, for example, nerve cells such as PC-12 cells, generally do not survive when insufficient serum is present. The use of insufficient serum in the growth medium to culture cells is referred to as "serum deprivation conditions" and includes, for example, from 0% to about 4% serum. Nerve growth factor (NGF) can protect PC-12 and other nerve cells from the effects of serum deprivation conditions. PTK activity is determined by the extent to which a peptide or peptide derivative can protect cells, e.g., neuronal cells, from the consequences of serum deprivation. Specific conditions are provided in Example 3.

Generally, the activity of the PTK in the test mixture is assessed by making a quantitative measure of the cellular activity which the PTK controls. For example, if cells are being used in which the PTK controls cell proliferation (e.g., bovine endothelial capillary cells in the presence of basic fibroblast growth factor), then PTK activity is assessed by measuring cellular proliferation, for example, by comparing the number cells present after a given period of time with the number of cells originally present. If cells are being used in which the PTK controls cell differentiation (e.g., PC-12 cells transfected with c-Src, see Alema et al., Nature 316:557 (1985)), activity is assessed by measuring the degree of differentiation (e.g., the degree to which neurites are extended and the degree to which markers of neuronal differentiation are expressed in PC-12 cells transfected with c-Src; see Alema et al., and the degree to which the formation of mesoderm in developing Xenopus embroya cells is induced; see Burgess and Maciag, Ann. Rev. Biochem., 58:575 (1989) and Dionne et al., WO 92/00999). Activity can also be assessed by the extent to which the gene expression, cell morphology or cellular phenotype is altered, e.g., by assessing the degree to which cell shape is altered, the degree to which the cells assume a spindle-like structure, alteration in gene expression or a change in the response to external stimuli (see Example 5 for conditions suitable for assessing changes in cell shape). If serum deprivation conditions are used, then activity is assessed by the extent of cell survival. Greater cell survival in the test mixture compared with the control indicates that peptide or peptide derivative is able to prevent apoptosis (programmed cell death).

Specific examples of conditions suitable for determining the activity of PTKs by assessing cell proliferation are provided in Examples 2 and 4. Specific examples of serum deprivation conditions suitable for determining the activity of PTKs by assessing cell survival are provided in Example 3.

It is to be understood that the assay described hereinabove for determining whether a peptide or peptide derivative modulates a cellular activity or function under the control of a PTK can be performed with cells other than those specifically described herein. PTKs not yet discovered or PTKs whose function is not yet known can also be used in this assay, once it has been determined which cellular functions or activities they control. These PTKs are also within the scope of the present invention.

The present invention is also directed to a method of modulating the activity of a protein tyrosine kinase in a subject. A "subject" is preferably a human, but can also be an animal in need of treatment, e.g., veterinary animals (e.g., dogs, cats, and the like), farm animals (e.g., cows, pigs, horses and the like) and laboratory animals (e.g., rats, mice, guinea pigs and the like).

The activity of a PTK in a subject can be modulated for the purpose of treating certain diseases, for example, proliferative diseases such as cancer, nonmalignant proliferative disease such as arteriosclerosis, psoriasis and inflammatory responses such as septic shock. For example, cancer can be treated by anti-angiogenic therapies. Inhibition of c-Met or tyrosine kinase receptors which respond to fibroblast growth factor (FGF), or vascular endothelial growth factor (VEGF) decreases angiogenesis. As a result, cancers can be treated by administering a therapeutically effective amount of a peptide or peptide derivative which results in decreased activity of c-Met or tyrosine kinase receptors which respond to FGF or VEGF. In addition, RET is involved in certain thyroid cancers; therapeutically effective amounts of peptides or peptide derivatives which modulate the activity of RET can be used to treat these thyroid cancers.

Restenosis is caused by vascular smooth muscle proliferation in response to, for example, vascular injury caused by balloon catheterization. Vascular smooth muscle proliferation is also a cause of arteriosclerosis. Vascular smooth muscle proliferation is a result of, for example, inhibition of Csk and/or stimulation of tyrosine kinase receptors which respond to FGF or platelet derived growth factor (PDGF). Thus, restenosis and arteriosclerosis can be treated with a therapeutically effective amount of a peptide or peptide derivativelwhich inhibits tyrosine kinase receptors which respond to FGF or PDGF or which activate Csk.

FGF has also been implicated in psoriasis, arthritis and benign prostatic hypertrophy (Dionne et al., WO 92/00999). These conditions can. be treated with HJ peptides from PTKs which respond to FGF.

Src activity is responsible, at least in part, for bone resorption. Thus, osteoporosis can be treated with a therapeutically effective amount of a peptide or peptide derivative which inhibits Src activity or which activates Csk.

Lyn and Hck are activated during the non-specific immune response which occurs in individuals with arthritis which occurs in individuals as a result of allergic responses. Lyn is also activated in individuals with septic shock. Thus, these conditions can be treated with a therapeutically effective amount of a peptide or peptide derivative which inhibits the activity of these PTKs.

Lck is expressed in T cells and is activated during a T cell immune response. Similarly, Lyn is expressed in B cells and activated during a B cell immune response. Thus, conditions which are caused by overactivation of T cells or B cells can be treated by administering a therapeutically effective amount of a peptide or peptide derivative which inhibits Lck or Lyn, respectively. Conditions which are caused by underactivation of T cells or B cells can be treated by administering a therapeutically effective amount of a peptide or peptide derivative which stimulates Lck or Lyn, respectively. In addition, a severe reduction of the B cell progenitor kinase leads to human X-linked agammaglobulinemia, which can be treated by administering a therapeutically effective amount of a peptide or peptide derivative which stimulates B cell progenitor kinase.

Decreased function of other PTKs can also be lead to disease. For example, a decrease in the activity of insulin receptor tyrosine kinase (RTK) is a cause of various types of diabetes. These types of diabetes can be treated by administering a therapeutically effective amount of a peptide or peptide derivative which increases the activity of the insulin RTK.

Based on methods disclosed herein, peptides and peptide derivatives can be designed to modulate the activity of PTKs whose HJ loop has been sequenced and whose cellular function is known. As a consequence, peptides and peptide derivatives can be designed to affect (increase or decrease) those cellular functions. It is possible that future research will reveal that certain disease conditions, whose underlying causes are presently unknown, are brought about by the overactivity or underactivity of cellular functions controlled by PTKs. These diseases can be treated by administering peptides which are peptide derivatives of the HJ loop of the overactive or underactive PTK. Suitable peptides and peptide derivatives can be identified by methods disclosed herein. These methods of treatment, peptides and peptide derivatives are encompassed within the scope of the present invention.

A "therapeutically effective amount" is the quantity of compound which results in an improved clinical outcome as a result of the treatment compared with a typical clinical outcome in the absence of the treatment. An "improved clinical outcome" refers, for, example, to a longer life expectancy, fewer complications, fewer symptoms, less physical discomfort and/or fewer hospitalizations as a result of the treatment.

With respect to cancer, an "improved clinical outcome" includes a longer life expectancy. It can also include slowing or arresting the rate of growth of a tumor, causing a shrinkage in the size of the tumor, a decreased rate of metastasis or an improved quality of life (e.g., a decrease in physical discomfort or an increase in mobility).

With respect to restenosis and arteriosclerosis, "an improved clinical outcome" includes, for example, a longer life expectancy or a decrease in the rate of arterial occlusion. It can also include an improved quality of life (e.g., a decrease in physical discomfort, an increase in mobility and a decrease in the frequency and/or length of hospitalization).

With respect to osteoporosis, "an improved clinical outcome" includes, for example, a decrease in the rate of bone deterioration, an increase in the rate of bone formation and/or an improved quality of life (e.g., a decrease in physical discomfort, an increase in mobility and a decrease in the frequency and/or length of hospitalization).

With respect to modulation of the immune system, "an improved clinical outcome" refers to an increase in the magnitude of the immune response in the individual, if the individual has a disease involving immune suppression. For example, for individuals with x-linked agammaglobulinemia, an if improved clinical outcome includes an increase in the immunoglobulin level. "An improved clinical outcome" for individuals with suppressed immune systems can also refer to a lesser susceptibility to infectious diseases. For diseases involving an overactive immune system, "an improved clinical outcome" refers to a decrease in the magnitude of the immune response. In both cases, an improved clinical outcome can also involve an improvement in the quality of life, as described above.

With respect to diabetes, an improved clinical outcome refers to a longer life expectancy, a reduction in the complications of the disease (e.g., neuropathy, retinopathy, nephropathy and degeneration of blood vessels) and an improved quality of life, as described above.

The amount of peptide or peptide derivative administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the peptide or peptide derivative can range from about 1 mg per day to about 1000 mg per day for an adult. Preferably, the dosage ranges from about 1 mg per day to about 100 mg per day.

Parenteral administration can include, for example, systemic administration, such as by intramuscular, intravenous, subcutaneous, or intraperitoneal injection. Peptides or peptide derivatives which resist proteolysis can be administered orally, for example, in capsules, suppositories, suspensions or tablets.

The peptide or peptide derivative can be administered to the individual in conjunction with an acceptable pharmaceutical carrier as part of a pharmaceutical composition for treating cancer, arteriosclerosis, osteoporosis or the other diseases discussed above. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., *Controlled Release of Biological Active Agents*, John Wiley and Sons, 1986).

The HJ loop peptides of the present invention are derived from an array which is linear in the native protein. Therefore, they can be useful in the preparation of specific antibodies against PTKs. Moreover, since the HJ loop sequence is unique to each sub-family of PTK, anti-HJ loop antibodies can be specifically used to isolate distinct sub-families of PTK.

Suitable antibodies against an HJ loop peptide can be prepared by conjugating to a suitable carrier, such as keyhole limpet hemocyanin or serum albumin; polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, Antibodies: *A Laboratory Manual*, (Cold Spring Harbor Laboratory: Cold Spring Harbor, N.Y.); *Current Protocols In Molecular Biology*, Vol. 2 (Supplement 27, Summer 1994), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be a selected by a suitable assay (e.g., ELISA).

Antibodies, including monoclonal antibodies, against HJ loop peptides have a variety of uses. For example, those against or reactive with the protein from which the HJ peptides was derived, and preferably which bind specifically to said protein, can be used to identify and/or sort cells exhibiting that protein on the cell surface (e.g., by fluorescence activated cell sorting or histological analyses). Monoclonal antibodies specific for the protein can also be used to detect and/or quantitate the protein expressed on the surface of a cell or present in a sample (e.g., in an ELISA). Alternatively, the antibodies can be used to determine if an intracellular PTK is present in the cytoplasm of the cell. A cleared lysate of the cell is generated (for example, by treating the cells with sodium hydroxide (0.2 N) and sodium dodecyl sulfate (1%), centrifugating and separating the supernatant from the pellet) followed by treatment with anti-HJ loop antibody specific for the PTK. The cleared lysate is then analyzed, for example, by Western blotting or immunoprecipitation for complexes between PTK and antibody. Some PTKs become membrane-bound or cytoskeleton-associated following stimulation. Anti-HJ loop antibodies can be also utilized for the study of the intracellular distribution (compartmentalization) of various sub-families of PTKs under various physiological conditions via the application of conventional immunocytochemistry such as immunofluorescence, immunoperoxidase technique and immunoelectron microscopy, in conjunction with the specific anti-HJ loop antibodies.

Antibodies reactive with the immunogen are also useful. For example, they can be used to detect and/or quantitate immunogen in a sample, or to purify immunogen (e.g., by immunoaffinity purification).

The HJ loop within PTKs plays a key role in regulating the activity of PTKs, as is evidenced by the fact that the peptides and peptide derivatives of the present invention have such a dramatic effect on the activity of PTKs. The HJ loop peptides of the present invention can also be used to identify ligands which interact with the HJ loops of specific PTKS. For example, an affinity column can be prepared to which a specific HJ loop peptide is covalently attached, directly or via a linker. This column, in turn, can then be utilized for the isolation and identification of specific ligands which bind the HJ loop peptide and which will also likely bind the PTK from which the HJ loop peptide was derived. The ligand can then be eluted from the column, characterized and tested for its effect on PTK activity and the cellular functions which the PTK controls.

Serine/threonine kinases are another class of protein kinases. They act as intracellular and, in the case of G protein-coupled receptor kinases, membrane bound proteins involved in cellular signal transduction. Binding of ligand to a serine/threonine kinase results in signal transduction to the interior of the cell, initiated by the phosphorylation of serine or threonine residues of intracellular proteins by the kinase. As with PTKs, serine/threonine kinases control cellular functions by means of this phosphorylation mechanism (Hardie, "Cellular Functions of Protein Kinases", in Hardie and Hanks (ed.) The Protein Kinase *FactsBook*, Academic Press 1995). Serine/threonine kinases have a high degree of homology with protein tyrosine kinases, including an HJ loop. Consequently, the activity of serine/threonine kinases, and the cellular functions which they control, can be modulated with peptides which are peptide derivatives of their HJ loops, as discussed above for PTKs. Peptides and peptide derivatives of the HJ loop of serine/threonine kinases and methods of use thereof are disclosed in the concurrently filed and co-pending application entitled "SHORT PEPTIDES WHICH SELECTIVELY MODULATE THE ACTIVITY OF SERINE/THREONINE KINASES" (Attorney Docket No. CMCC-590, filed May 21, 1997), the teachings of which are incorporated into this application.

Peptide sequences in the compounds of the present invention can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48–267; and Barany and Merrifield, in The Peptides, E. Gross and J. Meienhofer, Eds., Academic Press, New York, 1980, pp. 3–285. Methods of solid phase peptide synthesis are described in Merrifield, R. B., *Science*, 232: 341 (1986); Carpino, L.A. and Han, G. Y., *J. Org. Chem.*, 37: 3404 (1972); and Gauspohl, H. et al., *Synthesis*, 5: 315 (1992)). The teachings of these references are incorporated herein by reference.

Methods of cyclizing compounds having peptide sequences are described, for example, in Lobl et al., WO 92/00995, the teachings of which are incorporated herein by reference in their entirety. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protection such as allyl (OAl) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd° and Acm is easily removed by iodine treatment.

The invention is illustrated by the following examples which are not intended to be limiting in any way.

Example 1

Preparation of HJ Peptides

The novel compounds of this invention can be synthesized utilizing a 430A Peptide Synthesizer from Applied Biosystems using F-Moc technology according to manufacturer's protocols. Other suitable methodologies for preparing peptides are known to person skilled in the art. See e.g., Merrifield, R. B., *Science*, 232: 341 (1986); Carpino, L. A., Han, G. Y., *J. Org. Chem.*, 37: 3404 (1972); Gauspohl, H., et al., *Synthesis*, 5: 315 (1992)). The teachings of which are incorporated herein by reference.

Rink Amide Resin [4(2',4' Dimethoxyphenyl-FMOC amino methyl) phenoxy resin] was used for the synthesis of C-amidated peptides. The alpha-amino group of the amino acid was protected by an FMOC group, which was removed at the beginning of each cycle by a weak base, 20% piperidine in N-methylpyrrolidone (NMP). After deprotection, the resin was washed with NMP to remove the piperidine. In situ activation of the amino acid derivative was performed by the FASTMOC Chemistry using HBTU (2(1-benzotriazolyl-1-yl)-1,1,3,3-tetramethyluronium) dissolved in HOBt (1-hydroxybenzotriazole) and DMF (dimethylformamide). The amino acid was dissolved in this solution with additional NMP. DIEA (diisopropylethylamine) was added to initiate activation. Alternatively, the activation method of DCC (dicyclohexylcarbodiimide) and HOBt was utilized to form an HOBt active ester. Coupling was performed in NMP. Following acetylation of the N-terminus (optional), TFA (trifluoroacetic acid) cleavage procedure of the peptide from the resin and the side chain protecting groups was applied using 0.75 g crystalline phenol; 0.25 ml EDT (1,2-ethandithiol); 0.5 ml thioanisole; 0.5 ml D.I. $H_2O$; 10 ml TFA.

Example 2

HJ Peptides Affect the Proliferation of Bovine Capillary Endothelial Cells In Vitro 96 well, flat bottom, tissue culture microtiter plates were precoated with gelatin (Difco) immediately prior to cell plating by adding 0.100 ml/well of freshly filtered 1% gelatin in glass double distilled water (DDW). The wells were incubated for about 1 hour at 37° C., and then the excess solution was removed by aspiration.

Culture medium was prepared from DMEM, penicillin (100 U/ml), streptomycin (100 μg/ml), glutamine (2 mM), 10% endotoxin free bovine calf serum (Hyclone) and 1 ng/ml of basic fibroblast growth factor (any commericial source).

A bovine capillary endothelial cell (BCE) suspension at $25 \times 10^3$ cells/ml was prepared in the above described culture medium and distributed 0.160 ml/well (about 4000 endothelial cells/well). BCE cells are obtained by procedures disclosed in Folkman et al. *Proc. Natl. Acad. Sci. USA* 76:5217 (1979).

A series of HJ peptide stock solutions was prepared by diluting a 10 mM solution of the HJ peptide in 100% DMSO with phosphate buffered saline (PBS)containing 0.1% BSA. The concentration of HJ peptide in each stock solution was adjusted to nine times the desired concentration of the HJ peptide in the assay mixture.

0.020 ml of each HJ peptide stock solution was added to the corresponding wells about 2 hours after BCE plating, with six replicates for each concentration. In addition, BSA solution with no added HJ peptide was used as a control. The wells were incubated for 72–80 hours at 37° C. in a 10% $CO_2$ humidified incubator.

The plates were labeled and the medium discarded. Each plate was then washed one time with PBS (0.200 ml/well). The wells were then fixed by washing with 100% ethanol (0.200 ml/well for 5 minutes). The ethanol was removed and the wells dried completely. Alternatively, the wells were fixed with 4% formaldehyde PBS (PBS buffered 10% formalin from Fisher Scientific; Catalog No. HC200-1) (0.12 ml/well) for at least 30 minutes. Fixing with formaldehyde enhances the O.D. compared with ethanol.

The wells were washed one time with borate buffer (0.1 M, pH 8.5). Freshly filtered 1% methylene blue solution (0.600 ml/well) was then added to the wells and incubated for 10 minutes at room temperature. The wells were then washed five times with tap water, after which the wells were dried completely. 0.200 ml/well of 0.1 N HCl (0.1 N) was added to extract the color. After extracting overnight, the O.D. was read at 630 nm to determine the number of cells per well. The procedure for counting cells is described in greater detail in Oliver et al., *J. of Cell Sci.*, 92:513 (1989), the teachings of which are incorporated herein by reference.

The results for a number of different HJ peptides are shown in Table 1. Also shown in Table 1 are the sequences of each HJ peptide tested and the subsequence of the HJ loop from which each HJ peptide is derived (subsequences of the HJ loop of Src (SEQ ID NO.: 53), Endoth (SEQ ID NO.: 51) and NGF-R (SEQ ID NO.: 52)).

HJ4 (SEQ ID NO.: 13), HJ12 (SEQ ID NO.: 25) and HJ13 (SEQ ID NO.: 26) are each peptide derivatives of the same subsequence of the HJ loop of Src. HJ4 inhibited BCE cell proliferation; HJ12 and HJ13 stimulated BCE cell proliferation. This result shows that a cellular activity under control of a PTK can be either stimulated or inhibited, depending on the sequence of the peptide derivative used.

HJ11 (SEQ ID NO.: 22) also inhibited BCE cell proliferation. HJ11 is a subsequence of a different section of the src HJ loop than HJ4, HJ11 and HJ13. This result shows that peptide derivatives of different sections of an HJ loop can be used to stimulate or inhibit cellular activities.

HJ7 (SEQ ID NO.: 17) is a peptide derivative of the HJ loop of Endoth. This HJ peptide also inhibits the proliferation of BCE cells. This result shows that a cellular activity may be controlled by a number of different PTKs and that it is possible to affect the cellular activity by a tpeptide derivative of the HJ loop of one of the PTKs that control the cellular activity.

TABLE 1

SUMMARY OF BCE RESPONSE TO HJ PEPTIDES

| SRC | E- | L- | V- | T- | K- | G- | R- | V- | P- | Y- | P- | G | Effect | μM | SEQ ID NO |
|---|---|---|---|---|---|---|---|---|---|---|---|---|---|---|---|
| HJ4 |  | L- | V- | T- | K- | G- | R- | V |  |  |  |  | Inhibition | 40 | 13 |
| HJ12 |  | L- | V- | T- | K- | G- | R- | V |  |  |  |  | S. stimulation | 10 | 25 |
| HJ13 |  | L- | V- | T- | K- | G- | R- | V |  |  |  |  | S. stimulation | 5 | 26 |
| HJ11 |  |  |  |  |  | G- | R- | V- | P- | F- | P- | G | Inhibition | 5 | 22 |
| HJ6 | E- | L- | V- | T- | K- | G- | R- | V- | P- | Y |  |  | No response | up to 10 | 16 |
| HJ8 |  | L- | V- | T- | K- | G- | R- | V- | P- | F- | P- | G | No response | up to 10 | 19 |

|  |  |  |  | T |  |  | T |  |  |  |  |  |  |  |  |
|---|---|---|---|---|---|---|---|---|---|---|---|---|---|---|---|
| Endoth | E- | I- | F- | S- | L- | G- | G- | S- | P- | Y- | P- | G | Effect | μM | 51 |
| HJ7 |  | I- | F- | S- | L- | G- | G- | S |  |  |  |  | S. stimulation | 5 | 17 |
| HJ15 |  |  |  |  |  | G- | G- | S- | P- | Y- | F- | G | No response | up to 10 | 28 |
| HJ9 |  | I- | F- | S- | L- | G- | G- | S- | P- | F- | P- | G | No response | up to 10 | 20 |

| NGF-R | E- | I- | F- | T- | Y- | G- | K- | Q- | F- | W- | Y- | Q | Effect | μM | 52 |
|---|---|---|---|---|---|---|---|---|---|---|---|---|---|---|---|
| HJ10 |  | I- | F- | T- | Y- | G- | K- | Q |  |  |  |  | No response | up to | 21 |
| HJ14 |  |  |  |  |  | G- | K- | Q- | P- | W- | Y- | Q | No response | up to | 27 |

*K = d-Lys; all peptides are N-Acetylated and C-Amidated

Example 3

HJ Peptides Derivatives of c-Src Protect PC-12 Cells From the Effects of Serum Deprivation PC-12 cells were assayed for cell proliferation in the presence of HJ4 and HJ8 according to the procedure described in Example 2 except that 1) the culture medium contained either 2% or 4% horse serum; 2) fibroblast growth factor was not added; and 3) the cells were incubated for eleven days. The cells were counted according to the method described in Example 2. Specifically, the cells were fixed and stained with methylene blue, after which the amount of bound methylene blue was determined. The amount of bound methylene blue measured by the absorbance at 600 nM corresponds to the number of cells present in the wells. The results are shown in Table 2:

TABLE 2

| O.D. AT 600 NM (corresponds to the relative cell number) | | | | | | |
|---|---|---|---|---|---|---|
| Horse Serum | HJ4 Concentration | | | HJ8 Concentration | | |
| concentration | 40 μM | 8 μM | 0 | 40 μM | 8 μM | 0 |
| 2% Horse Serum | 300 | 134 | 91 | 170 | 112 | 81 |
| 4% Horse Serum | 1,154 | 470 | 305 | 670 | 384 | 320 |

As can be seen, HJ4 and HJ8 both enhance neuronal cell survival.

Example 4

HJ Peptide Derivatives of Protein Tyrosine Kinases Modulate Proliferation of Endothelial Cells In Vitro Bovine endothelial aortic cells (referred to herein as "A19 cells") were obtained by procedures disclosed in Gospodorowicz et al. *Proc. Natl. Acad. Sci. USA* 73:4120 (1976). Mouse MS1 and SVR cells were obtained by the procedures disclosed in Arbiser et al., *Proc. Natl. Acad. Sci.* 94:861 (1997), the teachings of which are incorporated herein by reference.

The effect of HJ peptides on cell proliferation was assayed according to the procedure described in Example 2 except that fibroblast growth factor was not added. The cells were counted according to the method described in Example 2. Specifically, the cells were fixed and stained with methylene blue, after which the amount of bound methylene blue was determined. The amount of bound methylene blue measured by the absorbance at 600 nM corresponds to the number of cells present in the wells. The results are shown in Table 3.

TABLE 3

| Peptide | S.I.* ($\mu$M) for SVR Cells | S.I.* ($\mu$M) for MS1 Cells | S.I.* ($\mu$M) for A19 Cells |
|---|---|---|---|
| c-Src | | | |
| HJ4.2 | 40 | | |
| HJ4-Nitro | | 10 | |
| HJ11.1 | 10 | | |
| HJ20 | 40 | | |
| HJ20.1 | 10 | | |
| HJ21.1 | 10 | | |
| HJ22 | 40 | | |
| HJ30 | | | 40 |
| Lyn/Hck | | | |
| HJ24 | | | Inactive |
| HJ32 | | | 40 |
| c-Abl | | | |
| HJ25 | | | Inactive |
| HJ33 | 40 | | 40 |
| Csk | | | |
| HJ27 | | | 10 |
| HJ31 | | 10 | |
| C-Met | | | |
| HJ28 | | | 40 |
| FAK | | | |
| HJ34 | | 40 | |

*Concentration at which significant inhibition of cell proliferation was observed.

HJ peptide derivatives of c-Src, Lyn/Hck, c-Abl, Csk, c-Met and FAK were effective at inhibiting endothelial cell proliferation at concentrations as low as 10 $\mu$M.

Example 5

HJ Peptide Derivatives of Lyn/Hck Cause Changes in the Shape of Vascular Smooth Muscle Cells Bovine vascular smooth muscle cells (VSMC), obtained by procedures disclosed in Castellot et al., *J. Cell Biol.* 102:1979 (1986), were grown in culture and incubated with the HJ peptides HJ24 or HJ32, as described in Example 4. After 48 hours, these peptide derivatives demonstrated an outstanding ability to induce a change in the cell shape of the VSMC cells. The cells became elongated and assumed a spindle-like structure. HJ32 was active at 10 and 40 gM and HJ24 was active at 40 $\mu$M in causing these morphological changes.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A peptide capable of modulating the activity of a protein tyrosine kinase having a structure that includes the twelve subdomains and nine alpha helices that are characteristic of the protein tyrosine kinase superfamily, consisting of:

(a) a subsequence of an HJ-loop peptide, which subsequence consists of at least five contiguous amino acids of said HJ-loop peptide, and which subsequence peptide modulates the activity of the protein tyrosine kinase of which said HJ-loop peptide is a part, wherein said HJ-loop peptide is a peptide consisting of a sequence of about 20 amino acid residues of the protein tyrosine kinase between the middle of Subdomain IX and the middle of Subdomain X, beginning about five residues from the N-terminus of the F helix and extending to about five amino acid residues into the G helix, which amino acids correspond to a continuous stretch of the prototypical PKA-Cα in positions 229–248 of the PKA-Cα, and which HJ-loop peptide modulates the activity of the protein tyrosine kinase;

(b) a modified sequence peptide having a modified sequence of (a) in which up to two residues are each substituted by another amino acid residue or amino acid residue analog, which modified sequence peptide modulates the activity of the protein tyrosine kinase;

(c) a protected peptide (a) or (b) in which the N-terminus and/or the C-terminus is protected by a protecting group, which protected peptide modulates the activity of the protein tyrosine kinase; or (d) a cyclized peptide of (a), (b), or (c) which has been cyclized, which cyclized peptide modulates the activity of the protein tyrosine kinase.

2. A peptide in accordance with claim 1, consisting of a subsequence peptide of (a); a peptide of (a) in which the N-terminus and/or the C-terminus is protected by a protecting group, which protected peptide modulates the activity of the protein tyrosine kinase; or a peptide of (a) which has been cyclized, which cyclized peptide modulates the activity of the protein tyrosine kinase.

3. A peptide in accordance with claim 2, consisting of a subsequence peptide of (a).

4. A peptide in accordance with claim 1, consisting of a modified sequence peptide of (b); a peptide of (b) in which the N-terminus and/or the C-terminus is protected by a protecting group, which protected peptide modulates the activity of the protein tyrosine kinase; or a peptide of (b) which has been cyclized, which cyclized peptide modulates the activity of the protein tyrosine kinase.

5. A peptide in accordance with claim 4, consisting of a modified peptide of (b).

6. A peptide in accordance with claim 1, consisting of a protected peptide of (c).

7. A peptide in accordance with claim 6, consisting of a cyclized peptide of (d).

8. The peptide of claim 6, wherein the N-terminal amino acid is amidated and the C-terminal amino acid is acylated.

9. The peptide of claim 1, wherein the protein tyrosine kinase is a member of a protein tyrosine kinase family selected from the group consisting of Src, EGF-R, FGF-R, VEGF-R, HGF-R, PDGF-R, insulin receptor family and neurotrophin receptor family.

10. The peptide of claim 9, wherein the protein tyrosine kinase is from the src family of protein tyrosine kinases and is selected from the group consisting of c-Src, c-Yes, FYN, FGR, HCK, LYN, LCK and BLK.

11. The peptide of claim 1, wherein the protein tyrosine kinase is selected from group of protein tyrosine kinases consisting of RET, CSK, c-Met, c-Abl and FAK.

12. The peptide of claim 1, wherein the peptide is a heptapeptide.

13. The peptide of claim 12, wherein the peptide consists of the sequence Leu-Val-Thr-Xaa-Gly-Arg-Val (SEQ ID NO.: 45), wherein Xaa is selected from the group consisting of L-lysine, D-lysine, histidine, tyrosine, phenylalanine and arginine.

14. The peptide of claim 12, wherein the peptide consists of the sequence Gly-Arg-Val-Pro-Yaa-Pro-Zaa (SEQ ID NO.: 46), wherein:

(a) Yaa is selected from the group consisting of tyrosine, phenylalanine and tryptophane; and (b) Zaa is selected from the group consisting of glycine, alanine and arginine.

15. The peptide of claim 9, wherein the protein tyrosine kinase is from the EGF-R family of protein tyrosine kinases and is selected from the group consisting of EGFR, ErbB2, ErbB3 and ErB4.

16. The peptide of claim 9, wherein the protein tyrosine kinase is from the FGF-R family of protein tyrosine kinases and is selected from the group consisting of FGFR1, FGFR2, FGFR3 and FGFR4.

17. The peptide of claim 9, wherein the protein tyrosine kinase is from the VEGF-R family of protein tyrosine kinases and is selected from the group consisting of Flt1, Flt4 and Flk1.

18. The peptide of claim 9, wherein the protein tyrosine kinase is from the insulin receptor family of protein tyrosine kinases and is selected from the group consisting of INS-R, IRR and IGF1-R.

19. The peptide of claim 9, wherein the a protein tyrosine kinase is from the neurotrophin receptor family of protein tyrosine kinases and is selected from the group consisting of TrkA, TrkB and TrkC.

20. The peptide of claim 1, wherein the peptide has a sequence selected from the group of peptides consisting of HJ4 (SEQ ID NO.: 13), HJ4.2 (SEQ ID NO.: 14), HJ4Nitro (SEQ ID NO.: 15), HJ6 (SEQ ID NO.: 16), HJ7 (SEQ ID NO.: 17), HJ7.1 (SEQ ID NO.: 18), HJ8 (SEQ ID NO.: 19), HJ9 (SEQ ID NO.: 20), HJ10 (SEQ ID NO.: 21), HJ11 (SEQ ID NO.: 22), HJ11.1 (SEQ ID NO.: 23), HJ11Met (SEQ ID NO.: 24), HJ12 (SEQ ID NO.: 25), HJ13 (SEQ ID NO.: 26), HJ14 (SEQ ID NO.: 27), HJ15 (SEQ ID. NO.: 28), HJ18 (SEQ ID NO.: 29), HJ20, (SEQ ID NO.: 30), HJ20.1 (SEQ ID NO.: 31), HJ21.1 (SEQ ID NO.: 32), HJ22 (SEQ ID NO.: 33), HJ23.1 (SEQ ID NO.: 34), HJ24 (SEQ ID NO.: 1), HJ25 (SEQ ID NO.: 35), HJ27 (SEQ ID NO.: 36), HJ28 (SEQ ID NO.: 37), HJ29 (SEQ ID NO.: 48), HJ30 (SEQ ID NO.: 38), HJ31 (SEQ ID NO.: 39), HJ32 (SEQ ID NO.: 2), HJ33 (SEQ ID NO.: 40), HJ34 (SEQ ID NO.: 41), HJ40 (SEQ ID NO.: 47), Lena 1 (SEQ ID NO.: 42), Lena 2 (SEQ ID NO.: 43) and J29 (SEQ ID NO.: 44).

21. A peptide having the sequence of a peptide selected from the group consisting of HJ4 (SEQ ID NO.: 13), HJ4.2 (SEQ ID NO.: 14), HJ4Nitro (SEQ ID NO.: 15), HJ6 (SEQ ID NO.: 16), HJ7 (SEQ ID NO.: 17), HJ7.1 (SEQ ID NO.: 18), HJ8 (SEQ ID NO.: 19), HJ9 (SEQ ID NO.: 20), HJ10 (SEQ ID NO.: 21), HJ11 (SEQ ID NO.: 22), HJ11.1 (SEQ ID NO.: 23), HJ11Met (SEQ ID NO.: 24), HJ12 (SEQ ID NO.: 25), HJ13 (SEQ ID NO.: 26), HJ14 (SEQ ID NO.: 27), HJ15 (SEQ ID NO.: 28), HJ18 (SEQ ID NO.: 29), HJ20, (SEQ ID NO.: 30), HJ20.1 (SEQ ID NO.: 31), HJ21.1 (SEQ ID NO.: 32), HJ22 (SEQ ID NO.: 33), HJ23.1 (SEQ ID NO.: 34), HJ24 (SEQ ID NO.: 1), HJ25 (SEQ ID NO.: 35), HJ27 (SEQ ID NO.: 36), HJ28 (SEQ ID NO.: 37), HJ29 (SEQ ID NO.: 48), HJ30 (SEQ ID NO.: 38), HJ31 (SEQ ID NO.: 39), HJ32 (SEQ ID NO.: 2), HJ33 (SEQ ID NO.: 40), HJ34 (SEQ ID NO.: 41), HJ40 (SEQ ID NO.: 47), Lena 1 (SEQ ID NO.: 42), Lena 2 (SEQ ID NO.: 43) and J29 (SEQ ID NO.: 44), with the proviso that any one amino acid residue in the peptide can be substituted by another amino acid residue or amino acid residue analog.

22. A peptide consisting of a sequence of amino acids $AA_1$ through $AA_{20}$, or a subsequence thereof consisting of at least five contiguous amino acids thereof, wherein:

$AA_1$ is threonine or tryptophan;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of leucine, isoleucine, methionine and valine;

$AA_4$ is selected from the group consisting of methionine, threonine, serine, valine, isoleucine and leucine;

$AA_5$ is threonine or serine;

$AA_6$ is selected from the group consisting of ornithine, lysine, histidine, tyrosine, arginine, N-nitroarginine, β-cycloarginine, γ-hydroxyargine, N-amidinocitruline and 2-amino-4-guanidinobutanoic acid;

49

AA$_7$ is glycine or alanine;

AA$_8$ is selected from the group consisting of arginine, N-nitroarginine, β-cycloarginine, γ-hydroxyargine, N-amidinocitruline, 2-amino-4-guanidinobutanoic acid and lysine;

AA$_9$ is selected from the group consisting of valine, isoleucine, leucine and methionine;

AA$_{10}$ is proline;

AA$_{11}$ is selected from the group consisting of tyrosine, phenylalanine and tryptophan;

AA$_{12}$ is proline;

AA$_{13}$ is glycine or alanine;

AA$_{14}$ is selected from the group consisting of methionine, arginine, N-nitroarginine, β-cycloarginine, γ-hydroxyargine, N-amidinocitruline and 2-amino-4-guanidinobutanoic acid;

AA$_{15}$ is selected from the group consisting of valine, asparagine, threonine and serine;

AA$_{16}$ is asparagine or lysine;

AA$_{17}$ is selected from the group consisting of arginine, N-nitroarginine, β-cycloarginine, γ-hydroxyargine, N-amidinocitruline, 2-amino-4-guanidinobutanoic acid alanine, and proline;

AA$_{18}$ is selected from the group consisting of glutamine, asparagine, glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of valine, isoleucine, leucine and methionine; and AA$_{20}$ is selected from the group consisting of leucine, isoleucine, methionine and valine.

23. The peptide of claim 22, wherein said sequence is that of SEQ ID NO:3 or SEQ ID NO:4, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 22.

24. The peptide of claim 22, wherein said sequence is that of SEQ ID NO:3, or a subsequence thereof comprising at least five contiguous amino acids thereof, with the proviso that any one amino acid in the sequence AA$_1$ through AA$_{20}$ or the subsequence thereof may vary among the variations specified for such residue in claim 22.

25. The peptide of claim 23 or claim 24, wherein the peptide comprises an eight amino acid subsequence selected from the group consisting of AA$_3$ through AA$_{10}$, AA$_7$ through AA$_{14}$ and AA$_{11}$ through AA$_{18}$.

26. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is selected from the group consisting of glutamic acid, aspartic acid and an aliphatic, substituted aliphatic, benxyl, substituted benzyl, aromatic or substituted aromatic ester of glutamic acid or aspartic acid;

AA$_3$ is selected from the group consisting of valine, leucine, isoleucine and methionine;

AA$_4$ is selected from the group consisting of tyrosine, phenylalanine and tryptophan;

AA$_5$ is threonine or serine;

AA$_6$ is tyrosine, phenylalanine or tryptophan;

AA$_7$ is glycine or alanine;

50

AA$_8$ is selected from the group consisting of arginine, N-nitroarginine, β-cycloarginine, γ-hydroxyargine, N-amidinocitruline, 2-amino-4-guanidinobutanoic acid, ornithine, and lysine;

AA$_9$ is valine or alanine;

AA$_{10}$ is proline;

AA$_{11}$ is selected from the group consisting of tyrosine, phenylalanine and tryptophan;

AA$_{12}$ is proline;

AA$_{13}$ is selected from the group consisting of ornithine, arginine, N-nitroarginine, β-cycloarginine, γ-hydroxyargine, N-amidinocitruline, 2-amino-4-guanidinobutanoic acid and lysine;

AA$_{14}$ is selected from the group consisting of valine, methionine, isoleucine and leucine;

AA$_{15}$ is selected from the group consisting of proline, threonine and serine;

AA$_{16}$ is selected from the group consisting of leucine, isoleucine, valine and methionine;

AA$_{17}$ is selected from the group consisting of ornithine, lysine, arginine, N-nitroarginine, β-cycloarginine, γ-hydroxyargine, N-amidinocitruline and 2-amino-4-guanidinobutanoic acid;

AA$_{18}$ is selected from the group consisting of asparagine, glutamine, glutamic acid, aspartic acid, and an aliphatic, substituted aliphatic, benzyl, substituted benzyl or substituted aromatic ester of aspartic acid or glutamic acid;

AA$_{19}$ is selected from the group consisting of valine, isoleucine, leucine and methionine; and AA$_{20}$ is selected from the group consisting of leucine, isoleucine, methionine and valine.

27. The peptide of claim 26, wherein said sequence is that of SEQ ID NO:5, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 26.

28. The peptide of claim 26, wherein said sequence is that of SEQ ID NO:5, or a subsequence thereof comprising at least five contiguous amino acids thereof, with the proviso that any one amino acid in the sequence AA$_1$ through AA$_{20}$ or the subsequence thereof may vary among the variations specified for such residue in claim 26.

29. The peptide of claim 27 or claim 28, wherein the peptide comprises an eight amino acid subsequence selected from the group consisting of AA$_3$ through AA$_{10}$, AA$_7$ through AA$_{14}$ and AA$_{11}$ through AA$_{18}$.

30. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is glutamic acid or an aliphatic, substituted aliphatic, benzyl, substituted benzyl, aromatic or aromatic ester of glutamic acid;

AA$_3$ is selected from the group consisting of isoleucine, leucine, alanine and methionine;

AA$_4$ is selected from the group consisting of alanine, glycine and valine;

AA$_5$ is threonine or serine;

AA$_6$ is selected from the group consisting of tyrosine, phenylalanine and tryptophan;

AA$_7$ is glycine or alanine;

AA$_8$ is selected from the group consisting of methionine, valine, leucine and isoleucine;

AA$_9$ is serine or threonine;

AA$_{10}$ is proline;

AA$_{11}$ is selected from the group consisting of tyrosine, phenylalanine and tryptophan;

AA$_{12}$ is proline;

AA$_{13}$ is glycine or alanine;

AA$_{14}$ is selected from the group consisting of methionine, isoleucine, valine and leucine;

AA$_{15}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{16}$ is selected from the group consisting of leucine, isoleucine, proline, lysine, ornithine, arginine, N-nitroarginine, β-cycloarginine, γ-hydroxyarginine, N-amidinocitruline and 2-amino-4-guanidinobutanoic acid;

AA$_{17}$ is serine or threonine;

AA$_{18}$ is selected from the group consisting of glutamine, asparagine, glutamicacid, aspartic acid and an aliphatic, substituted aliphatic, benzyl, substituted benzyl, aromatic or substituted aromatic ester of glutamic acid or aspartic acid;

AA$_{19}$ is selected from the group consisting of valine, isoleucine, leucine and methionine; and AA$_{20}$ is selected from the group consisting of tyrosine, phenylalanine and tryptophan.

31. The peptide of claim 30, wherein said, sequence is that of SEQ ID NO:6, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 30.

32. The peptide of claim 30, wherein said sequence is that of SEQ ID NO:6, or a subsequence thereof comprising at least five contiguous amino acids thereof, with the proviso that any one amino acid in the sequence AA$_1$ through AA$_{20}$ or the subsequence thereof may vary among the variations specified for such residue in claim 30.

33. The peptide of claim 31 or claim 32, wherein the peptide comprises an eight amino acid subsequence selected from the group consisting of AA$_3$ through AA$_{10}$, AA$_7$ through AA$_{14}$ and AA$_{11}$ through AA$_{18}$.

34. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of leucine, isoleucine, valine and methionine;

AA$_4$ is selected from the group consisting of methionine, leucine, isoleucine and valine;

AA$_5$ is threonine or serine;

AA$_6$ is selected from the group consisting of tyrosine, lysine, arginine, ornithine, N-nitroarginine, β-cycloarginine, γ-hydroxyarginine, N-amidinocitruline and 2-amino-4-guanidinobutanoic acid;

AA$_7$ is glycine or alanine;

AA$_8$ is glycine or alanine;

AA$_9$ is selected from the group consisting of proline, serine and threonine;

AA$_{10}$ is proline;

AA$_{11}$ is selected from the group consisting of tyrosine, phenylalanine and tryptophan;

AA$_{12}$ is proline;

AA$_{13}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{14}$ is selected from the group consisting of valine, methionine, isoleucine and leucine;

AA$_{15}$ is selected from the group consisting of glutamine, asparagine, glutamic acid, aspartic acid and an aliphatic, substituted aliphatic, benzyl, substituted benzyl, aromatic or substituted aromatic ester of glutamic acid or aspartic acid;

AA$_{16}$ is threonine or proline;

AA$_{17}$ is selected from the group consisting of phenylalanine, tyrosine and tryptophan;

AA$_{18}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of valine, isoleucine, leucine and methionine; and AA$_{20}$ is selected from the group consisting of threonine, serine and C-agitated derivatives thereof.

35. The peptide of claim 34, wherein said sequence is that of SEQ ID NO:7, or a subsequence thereof comprising at least five contiguous amino acids thereof, with the proviso that up to two amino acids in the sequence AA$_1$ through AA$_{20}$ or the subsequence thereof c an each vary among the variations specified for such residue in claim 34.

36. The peptide of claim 34, wherein said sequence is that of SEQ ID NO:7, or a subsequence thereof comprising at least five contiguous amino acids thereof, with the proviso that any one amino acid in the sequence AA$_1$ through AA$_{20}$ or the subsequence thereof m ay vary among the variations specified for such residue in claim 34.

37. The peptide of claim 35 or claim 36, wherein the peptide comprises an eight amino acid subsequence selected from the group consisting of AA$_3$ through AA$_{10}$, AA$_7$ through AA$_{14}$ and AA$_{11}$ through AA$_{18}$.

38. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of leucine, isoleucine, methionine and valine;

AA$_4$ is selected from the group consisting of methionine, leucine, isoleucine and valine;

AA$_5$ is selected from the group consisting of methionine, valine, isoleucine and leucine;

AA$_6$ is selected from the group consisting of histidine, lysine and ornithine;

AA$_7$ is glycine or alanine;

AA$_8$ is selected from the group consisting of valine, alanine and glycine;

AA$_9$ is selected from the group consisting of lysine, ornithine, arginine, N-nitroarginine, β-cycloarginine, γ-hydroxyarginine, N-amidinocitruline and 2-amino-4-guanidinobutanoic acid;

AA$_{10}$ is proline;

AA$_{11}$ is selected from the group consisting of tyrosine, phenylalanine and tryptophan;

AA$_{12}$ is glutamine or proline;

AA$_{13}$ is glycine or alanine;

AA$_{14}$ is selected from the group consisting of valine, isoleucine, leucine and alanine;

AA$_{15}$ is selected from the group consisting of lysine, ornithine, arginine, N-nitroarginine, β-cycloarginine, γ-hydroxyarginine, N-amidinocitruline and 2-amino-4-guanidinobutanoic acid;

AA$_{16}$ is selected from the group consisting of glutamine, asparagine, glutamic acid, aspartic acid and an aliphatic, substituted aliphatic, benzyl, substituted benzyl, aromatic or substituted aromatic ester of glutamic acid or aspartic acid;

AA$_{17}$ is selected from the group consisting of glutamine, asparagine, glutamic acid, aspartic acid and an aliphatic, substituted aliphatic, benzyl, substituted benzyl, aromatic or substituted aromatic ester of aspartic acid and glutamic acid;

AA$_{18}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of valine, isoleucine, leucine and methionine; and AA$_{20}$ is selected from the group consisting of valine, isoleucine, leucine, methionine and C-agitated derivatives thereof.

39. The peptide of claim 38, wherein said sequence is that of SEQ ID NO:8, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 38.

40. The peptide of claim 38, wherein said siquence is that of SEQ ID NO:8, or a subsequence thereof comprising at least five contiguous amino acids thereof, with the proviso that any one amino acid in the sequence AA$_1$ through AA$_{20}$ or the subsequence thereof may vary among the variations specified for such residue in claim 38.

41. The peptide of claim 39 or claim 40, wherein the peptide comprises an eight amino acid subsequence selected from the group consisting of AA$_3$ through AA$_{10}$, AA$_7$ through AA$_{14}$ and AA$_{11}$ through AA$_{18}$.

42. A peptide consisting of a sequence of amino acids AA$_1$ through AA$_{20}$, or a subsequence thereof consisting of at least five contiguous amino acids thereof, wherein:

AA$_1$ is tryptophan or methionine;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of leucine, isoleucine, methionine and valine;

AA$_4$ is selected from the group consisting of methionine, valine, isoleucine and leucine;

AA$_5$ is threonine or serine;

AA$_6$ is selected from the group consisting of phenylalanine, tyrosine and tryptophan;

AA$_7$ is glycine or alanine;

AA$_8$ is selected from the group consisting of arginine, N-nitroarginine, β-cycloarginine, γ-hydroxyarginine, N-amidinocitruline, 2-amino-4-guanidinobutanoic acid, lysine and ornithine;

AA$_9$ is selected from the group consisting of valine, isoleucine, leucine and methionine;

AA$_{10}$ is proline;

AA$_{11}$ is selected from the group consisting of tyrosine, phenylalanine and tryptophan;

AA$_{12}$ is proline;

AA$_{13}$ is glycine or alanine;

AA$_{14}$ is selected from the group consisting of methionine, arginine, N-nitroarginine, β-cycloarginine, γ-hydroxyarginine, N-amidinocitruline and 2-amino-4-guanidinobutanoic acid;

AA$_{15}$ is threonine or serine;

AA$_{16}$ is asparagine or glutamine;

AA$_{17}$ is selected from the group consisting of alanine, glycine and proline;

AA$_{18}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of valine, isoleucine, leucine and methionine; and AA$_{20}$ is selected from the group consisting of leucine, isoleucine, methionine and valine.

43. The peptide of claim 42, wherein said sequence is that of SEQ ID NO:9, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 42.

44. The peptide of claim 42, wherein said sequence is that of SEQ ID NO:9, or a subsequence thereof comprisign at least five contiguous amino acids thereof, with the proviso that any one amino acid in the sequence AA$_1$ through AA$_{20}$ or the subsequence thereof may vary among the variations specified for such residue in claim 42.

45. The peptide of claim 43 or claim 44, wherein the peptide comprises an eight amino acid subsequence selected from the group consisting of AA$_3$ through AA$_{10}$, AA$_7$ through AA$_{14}$ and AA$_{11}$ through AA$_{18}$.

46. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of leucine, isoleucine, methionine and valine;

AA$_4$ is selected from the group consisting of phenylalanine, tyrosine and tryptophan;

AA$_5$ is threonine or serine;

AA$_6$ is selected from the group consisting of leucine, isoleucine, valine and methionine;

AA$_7$ is glycine or alanine;

AA$_8$ is glycine or alanine;

AA$_9$ is serine or threonine;

AA$_{10}$ is proline;

AA$_{11}$ is selected from the group consisting of tyrosine, phenylalanine and tryptophan;

AA$_{12}$ is selected from the group consisting of proline, cysteine, serine and alanine;

AA$_{13}$ is glycine or alanine;

AA$_{14}$ is selected from the group consisting of rmethionine, valine, isoleucine and leucine;

AA$_{15}$ is selected from the group consisting of serine, threonine, methionine, proline, lysine, ornithine, glutamine and asparagine;

AA$_{16}$ is selected from the group consisting of cysteine, serine, methionine, valine, isoleucine and leucine;

AA$_{17}$ is selected from the group consisting of alanine, asparagine, aspartic acid and an aliphatic, substituted aliphatic, benzyl, substituted benzyl, aromatic or substituted aromatic ester of aspartic acid;

AA$_{18}$ is selected from the group consisting of threonine, serine, glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of threonine, leucine, glutamine, asparagine, glutamic acid, aspartic acid and an aliphatic substituted aliphatic, benzyl, substituted benzyl, aromatic or substituted aromatic ester of glutamic acid or aspartic acid; and AA$_{20}$ is selected from the group consisting of tyrosine, phenylalanine and tryptophan.

47. The peptide of claim 46, wherein said sequence is that of SEQ ID NO:10, or a subsequence thereof comprising at least five contiguous amino acids thereof, with the proviso that up to two amino acids in the sequence AA$_1$ through AA$_{20}$ the subsequence thereof can each vary among the variations specified for such residue in claim 46.

48. The peptide of claim 46, wherein said sepuence is that of SEQ ID NO:10, or a subsequence thereof comprising at least five contiguous amino acids thereof, with the proviso that any one amino acid in the sequence AA$_1$ through AA$_{20}$ or the subsequence thereof may vary among the variations specified for such residue in claim 46.

49. The peptide of claim 47 or claim 48, wherein the peptide comprises an eight amino acid subsequence selected from the group consisting of AA$_3$ through AA$_{10}$, AA$_7$ through AA$_{14}$ and AA$_{11}$ through AA$_{18}$.

50. A peptide consisting of a sequence of amino acids AA$_1$ through AA$_{20}$, or a subsequence thereof consisting of at least five contiguous amino acids thereof, wherein:

AA$_1$ is tryptophan;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of leucine, isoleucine, methionine and valine;

AA$_4$ is selected from the group consisting of phenylalanine, tyrosine and tryptophan;

AA$_5$ is threonine or serine;

AA$_6$ is selected from the group consisting of phenylalanine, tyrosine and tryptophan;

AA$_7$ is glycine or alanine;

AA$_8$ is lsyine or ornithine;

AA$_9$ is glutamine or asparagine;

AA$_{10}$ is proline;

AA$_{11}$ is selected from the group consisting of tyrosine, phenylalanine and tryptophan;

AA$_{12}$ is selected from the group consisting of tyrosine, phenylalanine and tryptophan;

AA$_{13}$ is glutamine or asparagine;

AA$_{14}$ is selected from the group consisting of leucine, isoleucine, methionine and valine;

AA$_{15}$ is serine or threonine;

AA$_{16}$ is glutamine or asparagine;

AA$_{17}$ is threonine or asparagine;

AA$_{18}$ is selected from the group consisting of glutamic acid, aspartic acid and an aliphatic, substituted aliphatic, benzyl, substituted benzyl, aromatic or substituted aromatic ester of glutamic acid or aspartic acid;

AA$_{19}$ is selected from the group consisting of glycine, alanine and valine; and AA$_{20}$ is selected from the group consisting of leucine, isoleucine, methionine and valine.

51. The peptide of claim 50, wherein said sequence is that of SEQ ID NO:11, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 50.

52. The peptide of claim 50, wherein said sequence is that of SEQ ID NO:11, or a subsequence thereof comprising at least five contiguous amino acids thereof, with the proviso that any one amino acid in the sequence AA$_1$ through AA$_{20}$ or the subsequence thereof may vary among the variations specified for such residue in claim 50.

53. The peptide of claim 51 or claim 52, wherein the peptide comprises an eight amino acid subsequence selected from the group consisting of AA$_3$ through AA$_{10}$, AA$_7$ through AA$_{14}$ and AA$_{11}$ through AA$_{18}$.

54. A peptide consisting of a sequence of amino acids AA$_1$ through AA$_{20}$, or a subsequence thereof consisting of at least five contiguous amino acids thereof, wherein:

AA$_1$ is glutamic acid, aspartic acid or an aliphatic, substituted aliphatic, benzyl, substituted benzyl, aromatic or substituted aromatic ester of glutamic acid or aspartic acid;

AA$_2$ is leucine, isoleucine, methionine or valine;

AA$_3$ is serine, threonine or proline;

AA$_4$ is phenylalanine, tyrosine or tryptophan;

AA$_5$ is glutamic acid, aspartic acid or an aliphatic, substituted aliphatic, benzyl, substituted-benzyl, aromatic or substituted aromatic ester of glutamic acid or aspartic acid;

AA$_6$ is leucine, isoleucine, methionine or valine;

AA$_7$ is leucine, isoleucine, methionine or valine;

AA$_8$ is threonine or serine;

AA$_9$ is phenylalanine, tyrosine or tryptophan;

AA$_{10}$ is glycine or alanine;

AA$_{11}$ is serine, alanine, threonine or glycine;

AA$_{12}$ is lysine, ornithine, arginine, N-nitroarginine, β-cycloarginine, γ-hydroxyarginine, N-amidinocitruline or 2-amino-4-guanidinobutanoic acid;

AA$_{13}$ is proline;

AA$_{14}$ is tyrosine, phenylalanine or tryptophan;

AA$_{15}$ is glutamic acid, aspartic acid or an aliphatic, substituted aliphatic, benzyl, substituted benzyl, aromatic or substituted aromatic ester of glutamic acid or aspartic acid;

AA$_{16}$ is glycine or alanine;

AA$_{17}$ is leucine, isoleucine, methionine or valine;

AA$_{18}$ is proline;

AA$_{19}$ is glycine, alanine, serine or threonine; and

AA$_{20}$ is serine, arginine, N-nitroarginine β-cycloarginine, γ-hydroxyarginine, N-amidinocitruline or 2-amino-4-guanidinobutanoic acid.

55. The peptide of claim 54, wherein said sequence is that of SEQ ID NO:12, or a subsequence thereof comprising at least five contiguous amino acids thereof, with the proviso that up to two amino acids in the sequence AA$_1$ through AA$_{20}$ or the subsequence thereof can each vary among the variations specified for such residue in claim 54.

56. The peptide of claim 54, wherein said sequence is that of SEQ ID NO:12, or a subsequence thereof comprising at least five contiguous amino acids thereof, with the proviso that any one amino acid in the sequence AA$_1$ through AA$_{20}$ or the subsequence thereof may vary among the variations specified for such residue in claim 54.

57. The peptide of claim 55 or claim 56, wherein the peptide comprises an eight amino acid subsequence selected from the group consisting of AA$_3$ through AA$_{10}$, AA$_7$ through AA$_{14}$ and AA$_{11}$ through AA$_{18}$.

58. A protected or cyclized peptide capable of modulating the activity of a protein tyrosine kinase having a structure that includes the twelve subdomains and nine alpha helices that are characteristic of the protein tyrosine kinase superfamily, consisting of:
(a) an HJ-loop peptide consisting of a sequence of about 20 amino acid residues of the protein tyrosine kinase between the middle of Subdomain IX and the middle of Subdomain X, beginning about five residues from the N-terminus of the F helix and extending to about five amino acid residues into the G helix, which amino acids correspond to a continuous stretch of the prototypical PKA-Cα in positions 229–248 of the PKA-Cα, and which HJ-loop peptide modulates the activity of the protein tyrosine kinase;
(b) a subsequence peptide consisting of a subsequence of (a) consisting of at least five contiguous amino acids thereof, which subsequence peptide modulates the activity of the protein tyrosine kinase; or
(c) a modified sequence peptide having a modified sequence of (a) or (b) in which up to two residues are each substituted by another amino acid residue or amino acid residue analog, which modified sequence peptide modulates the activity of the protein tyrosine kinase;
which peptide of (a), (b) or (c) is (1) a protected peptide in which the N-terminus and/or the C-terminus is protected by a protecting group which facilitates transport of the peptide into a cell, which protected peptide modulates the activity of the protein tyrosine kinase, or
which peptide of (a), (b) or (c) or said protected peptide is (2) a cyclized peptide in which said peptide of (a), (b) or (c) or said protected peptide has been cyclized, which cyclized peptide modulates the activity of the protein tyrosine kinase.

59. A protected or cyclized peptide in accordance with claim 58, consisting of said protected peptide of (1).

60. A protected or cyclized peptide in accordance with claim 58, consisting of said cyclized peptide of (2).

61. A protected or cyclized peptide in accordance with claim 58, wherein said peptide which is protected or cyclized consists of an HJ-loop peptide of (a).

62. A protected peptide in accordance with claim 59, wherein said peptide which is protected consists of an HJ-loop peptide of (a).

63. A cyclized peptide in accordance with claim 60, wherein said peptide which is cyclized consists of an HJ-loop peptide of (a).

64. A protected or cyclized peptide in accordance with claim 58, wherein said peptide which is protected or cyclized consists of a subsequence peptide of (b).

65. A protected peptide in accordance with claim 59, wherein said peptide which is protected consists of subsequence peptide of (b).

66. A cyclized peptide in accordance with cliam 60, wherein said peptide which is cyclized consists of a subsequence peptide of (b).

67. A protected or cyclized peptide in accordance with claim 58, wherein said peptide which is protected or cyclized consists of a modified sequence peptide of (c).

68. A protected peptide in accordance with claim 59, wherein said peptide which is protected consists of a modified sequence peptide of (c).

69. A cyclized peptide in accordance with claim 60, wherein said peptide which is cyclized consists of a modified sequence peptide of (c).

70. The protected or cyclized peptide of claim 59, wherein the N-terminal amino acid is amidated and the C-terminal amino acid is acylated.

71. The protected or cyclized peptide of claim 1, wherein the protein tyrosine kinase is a member of a protein tyrosine kinase familyselected from the group consisting of Src, EGF-R, FGF-R, VEGF-R, HGF-R, PDGF-R, insulin receptor family and neurotrophin receptor family.

72. The protected or cyclized peptide of claim 71, wherein the protein tyrosine kinase is from the src family of protein tyrosine kinases and is selected from the group consisting of c-Src, c-Yes, FYN, FGR, HCK, LYN, LCK and BLK.

73. The protected or cyclized peptide of claim 58, wherein the protein tyrosine kinase is selected from group of protein tyrosine kinases consisting of RET, CSK, c-Met, c-Abl and FAK.

74. The protected or cyclized peptide of claim 64, wherein the subsequence peptide of (b) is a heptapeptide.

75. The protected or cyclized peptide of claim 74, wherein the subsequence peptide of (b) consists of the sequence Leu-Val-Thr-Xaa-Gly-Arg-Val (SEQ ID NO.: 45), wherein Xaa is selected from the group consisting of L-lysine, D-lysine, histidine, tyrosine, phenylalanine and arginine.

76. The protected or cyclized peptide of claim 74, wherein the subsequence peptide of (b) consists of the sequence Gly-Arg-Val-Pro-Yaa-Pro-Zaa (SEQ ID NO.: 46), wherein:
(a) Yaa is selected from the group consisting of tyrosine, phenylalanine and tryptophane; and
(b) Zaa is selected from the group consisting of glycine, alanine and arginine.

77. The protected or cyclized peptide of claim 71, wherein the protein tyrosine kinase is from the EGF-R family of protein tyrosine kinases and is selected from the group consisting of EGFR, ErbB2, ErbB3 and ErB4.

78. The protected or cyclized peptide of claim 71, wherein the protein tyrosine kinase is from the FGF-R family of protein tyrosine kinases and is selected from the group consisting of FGFR1, FGFR2, FGFR3 and FGFR4.

79. The protected or cyclized peptide of claim 71, wherein the protein tyrosine kinase is from the VEGF-R family of protein tyrosine kinases and is selected from the group consisting of Flt1, Flt4 and Flk1.

80. The protected or cyclized peptide of claim 71, wherein the protein tyrosine kinase is from the insulin receptor family of protein tyrosine kinases and is selected from the group consisting of INS-R, IRR and IGF1-R.

81. The protected or cyclized peptide of claim 71, wherein the protein tyrosine kinase is from the neurotrophin receptor family of protein tyrosine kinases and is selected from the group consisting of TrkA, TrkB and TrkC.

82. The protected or cyclized peptide of claim 58, wherein the peptide has a sequence selected from the group of peptides consisting of HJ4 (SEQ ID NO.: 13), HJ4.2 (SEQ ID NO.: 14), HJ4Nitro (SEQ ID NO.: 15), HJ6 (SEQ ID NO.: 16), HJ7 (SEQ ID NO.: 17), HJ7.1 (SEQ ID NO.: 18), HJ8 (SEQ ID NO.: 19), HJ9 (SEQ ID NO.: 20), HJ10 (SEQ ID NO.: 21), HJ11 (SEQ ID NO.: 22), HJ11.1 (SEQ ID NO.: 23), HJllMet (SEQ ID NO.: 24), HJ12 (SEQ ID NO.: 25), HJ13 (SEQ ID NO.: 26), HJ14 (SEQ ID NO.: 27), HJ15 (SEQ ID NO.: 28), HJ18 (SEQ ID NO.: 29), HJ20, (SEQ ID NO.: 30), HJ20.1 (SEQ ID NO.: 31), HJ21.1 (SEQ ID NO.: 32), HJ22 (SEQ ID NO.: 33), HJ23.1 (SEQ ID NO.: 34), HJ24 (SEQ ID NO.: 1), HJ25 (SEQ ID NO.: 35), HJ27 (SEQ ID NO.: 36), HJ28 (SEQ ID NO.: 37), HJ29 (SEQ ID NO.: 48), HJ30 (SEQ ID NO.: 38), HJ31 (SEQ ID NO.: 39), HJ32 (SEQ ID NO.: 2), HJ33 (SEQ ID NO.: 40), HJ34 (SEQ ID NO.: 41), HJ40 (SEQ ID NO.: 47), Lena 1 (SEQ ID NO.: 42), Lena 2 (SEQ ID NO.: 43) and J29 (SEQ ID-NO.: 44), or has a sequence which is that of one of said-peptides which has been modified wherein any one amino acid residue in the peptide is substituted by another amino acid residue or amino acid residue analog, which modified peptide modulates the activity of the protein tyrosine kinase.

83. The protected or cyclized peptide of claim 82, wherein the peptide of (a), (b) or (c) has a sequence selected from the group of peptides consisting of HJ4 (SEQ ID NO.: 13), HJ4.2 (SEQ ID NO.: 14), HJ4Nitro (SEQ ID NO.: 15), HJ6 (SEQ ID NO.: 16), HJ7 (SEQ ID NO.: 17), HJ7.1 (SEQ ID NO.: 18), HJ8 (SEQ ID NO.: 19), HJ9 (SEQ ID NO.: 20), HJ10 (SEQ ID NO.: 21), HJ11 (SEQ ID NO.: 22), HJ11.1 (SEQ ID NO.: 23), HJllMet (SEQ ID NO.: 24), HJ12 (SEQ ID NO.: 25), HJ13 (SEQ ID NO.: 26), HJ14 (SEQ ID NO.: 27), HJ15 (SEQ ID NO.: 28), HJ18 (SEQ ID NO.: 29), HJ20, (SEQ ID NO.: 30), HJ20.1 (SEQ ID NO.: 31), HJ21.1 (SEQ ID NO.: 32), HJ22 (SEQ ID NO.: 33), HJ23.1 (SEQ ID NO.: 34), HJ24 (SEQ ID NO.: 1), HJ25 (SEQ ID NO.: 35), HJ27 (SEQ ID NO.: 36), HJ28 (SEQ ID NO.: 37), HJ29 (SEQ ID NO.: 48), HJ30 (SEQ ID NO.: 38), HJ31 (SEQ ID NO.: 39), HJ32 (SEQ ID NO.: 2), HJ33 (SEQ ID NO.: 40), HJ34 (SEQ ID NO.: 41), HJ40 (SEQ ID NO.: 47), Lena 1 (SEQ ID NO.: 42), Lena 2 (SEQ ID NO.: 43) and J29 (SEQ ID NO.: 44).

84. A peptide in accordance with claim 6, wherein said protecting group is a group which facilitates transport of the peptide into a cell.

85. A method of modulating activity of a protein tyrosine kinase in a subject, comprising administering a therapeutically effective amount of a peptide capable of modulating the activity of a protein tyrosine kinase having a structure that includes the twelve subdomains and nine alpha helices that are characteristic of the protein tyrosine kinase superfamily, consisting of:

(a) an HJ-loop peptide consisting of a sequence of about 20 amino acid residues of the protein tyrosine kinase between the middle of Subdomain IX and the middle of Subdomain X, beginning about five residues from the N-terminus of the F helix and extending to about five amino acid residues into the G helix, which amino acids correspond to a continuous stretch of the prototypical PKA-Cα in positions 229–248 of the PKA-Cα, and which HJ-loop peptide modulates the activity of the protein tyrosine kinase;

(b) a subsequence peptide consisting of a subsequence of (a) consisting of at least five contiguous amino acids thereof, which subsequence peptide modulates the activity of the protein tyrosine kinase;

(c) a modified sequence peptide having a modified sequence of (a) or (b) in which up to two residues are each substituted by another amino acid residue or amino acid residue analog, which modified sequence peptide modulates the activity of the protein tyrosine kinase;

(d) a protected peptide (a), (b) or (c) in which the N-terminus and/or the C-terminus is protected by a protecting group, which protected peptide modulates the activity of the protein tyrosine kinase; or (e) a cyclized peptide of (a), (b), (c) or (d) which has been cyclized, which cyclized peptide modulates the activity of the protein tyrosine kinase.

86. A method of modulating activity of a protein tyrosine kinase in a subject, comprising administering a therapeutically effective amount of a protected or cyclized peptide in accordance with claim 58.

87. A method of modulating activity of a protein tyrosine kinase in a subject, comprising administering a therapeutically effective amount of a peptide in accordance with claim 1.

* * * * *

SEQUENCE LISTING

```
<160> NUMBER OF SEQ ID NOS: 53

<210> SEQ ID NO 1
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: Ac-Isoleucine
<221> NAME/KEY: MOD_RES
<222> LOCATION: (7)..(7)
<223> OTHER INFORMATION: Isoleucine-NH2

<400> SEQUENCE: 1

Ile Val Thr Tyr Gly Lys Ile
1               5

<210> SEQ ID NO 2
<211> LENGTH: 7
```

```
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: Ac-Isoleucine
<221> NAME/KEY: MOD_RES
<222> LOCATION: (7)..(7)
<223> OTHER INFORMATION: Isoleucine-NH2

<400> SEQUENCE: 2

Ile Val Thr Tyr Gly Arg Ile
1               5

<210> SEQ ID NO 3
<211> LENGTH: 20
<212> TYPE: PRT
<213> ORGANISM: Artificial Sequence
<220> FEATURE:
<223> OTHER INFORMATION: synthetic

<400> SEQUENCE: 3

Thr Glu Leu Thr Thr Lys Gly Arg Val Pro Tyr Pro Gly Met Val Asn
1               5                  10                  15

Arg Glu Val Leu
            20

<210> SEQ ID NO 4
<211> LENGTH: 20
<212> TYPE: PRT
<213> ORGANISM: Artificial Sequence
<220> FEATURE:
<223> OTHER INFORMATION: synthetic

<400> SEQUENCE: 4

Thr Glu Ile Val Thr His Gly Arg Ile Pro Tyr Pro Gly Met Thr Asn
1               5                  10                  15

Pro Glu Val Ile
            20

<210> SEQ ID NO 5
<211> LENGTH: 20
<212> TYPE: PRT
<213> ORGANISM: Artificial Sequence
<220> FEATURE:
<223> OTHER INFORMATION: synthetic

<400> SEQUENCE: 5

Trp Glu Ile Tyr Ser Phe Gly Arg Val Pro Tyr Pro Arg Ile Pro Leu
1               5                  10                  15

Lys Asp Val Val
            20

<210> SEQ ID NO 6
<211> LENGTH: 20
<212> TYPE: PRT
<213> ORGANISM: Artificial Sequence
<220> FEATURE:
<223> OTHER INFORMATION: synthetic

<400> SEQUENCE: 6

Trp Glu Ile Ala Thr Tyr Gly Met Ser Pro Tyr Pro Gly Ile Asp Arg
1               5                  10                  15

Ser Gln Val Tyr
            20
```

<210> SEQ ID NO 7
<211> LENGTH: 20
<212> TYPE: PRT
<213> ORGANISM: Artificial Sequence
<220> FEATURE:
<223> OTHER INFORMATION: synthetic

<400> SEQUENCE: 7

Trp Glu Leu Met Thr Arg Gly Ala Pro Pro Tyr Pro Asp Val Asn Thr
1               5                   10                  15

Phe Asp Ile Thr
            20

<210> SEQ ID NO 8
<211> LENGTH: 20
<212> TYPE: PRT
<213> ORGANISM: Artificial Sequence
<220> FEATURE:
<223> OTHER INFORMATION: synthetic

<400> SEQUENCE: 8

Trp Glu Ile Leu Met His Gly Val Lys Pro Phe Gln Gly Val Lys Asn
1               5                   10                  15

Asn Asp Val Ile
            20

<210> SEQ ID NO 9
<211> LENGTH: 20
<212> TYPE: PRT
<213> ORGANISM: Artificial Sequence
<220> FEATURE:
<223> OTHER INFORMATION: synthetic

<400> SEQUENCE: 9

Tyr Glu Ile Val Thr Tyr Gly Lys Ile Pro Tyr Pro Gly Arg Thr Asn
1               5                   10                  15

Ala Asp Val Met
            20

<210> SEQ ID NO 10
<211> LENGTH: 20
<212> TYPE: PRT
<213> ORGANISM: Artificial Sequence
<220> FEATURE:
<223> OTHER INFORMATION: synthetic

<400> SEQUENCE: 10

Trp Glu Ile Phe Ser Leu Gly Gly Thr Pro Tyr Pro Gly Met Met Val
1               5                   10                  15

Asp Glu Thr Phe
            20

<210> SEQ ID NO 11
<211> LENGTH: 20
<212> TYPE: PRT
<213> ORGANISM: Artificial Sequence
<220> FEATURE:
<223> OTHER INFORMATION: synthetic

<400> SEQUENCE: 11

Trp Glu Ile Phe Thr Tyr Gly Lys Gln Pro Trp Tyr Gln Leu Ser Asn
1               5                   10                  15

Thr Glu Ala Ile

-continued

```
<210> SEQ ID NO 12
<211> LENGTH: 20
<212> TYPE: PRT
<213> ORGANISM: Artificial Sequence
<220> FEATURE:
<223> OTHER INFORMATION: synthetic

<400> SEQUENCE: 12

Trp Glu Ile Val Thr Leu Gly Gly Asn Pro Tyr Pro Gly Ile Pro Pro
1               5                   10                  15

Glu Arg Leu Phe
            20

<210> SEQ ID NO 13
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (7)..(7)
<223> OTHER INFORMATION: Valine-NH2

<400> SEQUENCE: 13

Leu Val Thr Lys Gly Arg Val
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine

<400> SEQUENCE: 14

Leu Val Thr Lys Gly Arg Val
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (6)..(6)
<223> OTHER INFORMATION: N-Nitroarginine
<221> NAME/KEY: MOD_RES
<222> LOCATION: (7)..(7)
<223> OTHER INFORMATION: Valine-NH2

<400> SEQUENCE: 15

Leu Val Thr Lys Gly Arg Val
1               5

<210> SEQ ID NO 16
<211> LENGTH: 10
<212> TYPE: PRT
```

```
<210> SEQ ID NO 16
<211> LENGTH: 10
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Glutamic Acid
<221> NAME/KEY: MOD_RES
<222> LOCATION: (10)..(10)
<223> OTHER INFORMATION: Tyrosine-NH2

<400> SEQUENCE: 16

Glu Leu Val Thr Lys Gly Arg Val Pro Tyr
1               5                   10

<210> SEQ ID NO 17
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Isoleucine
<221> NAME/KEY: MOD_RES
<222> LOCATION: (7)..(7)
<223> OTHER INFORMATION: Serine-NH2

<400> SEQUENCE: 17

Ile Phe Ser Leu Gly Gly Ser
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (7)..(7)
<223> OTHER INFORMATION: Serine-NH2

<400> SEQUENCE: 18

Ile Phe Ser Leu Gly Gly Ser
1               5

<210> SEQ ID NO 19
<211> LENGTH: 11
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl -Leucine
<221> NAME/KEY: MOD_RES
<222> LOCATION: (11)..(11)
<223> OTHER INFORMATION: Glycine-NH2

<400> SEQUENCE: 19

Leu Val Thr Lys Gly Arg Val Pro Phe Pro Gly
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Isoleucine
```

```
<221> NAME/KEY: MOD_RES
<222> LOCATION: (11)..(11)
<223> OTHER INFORMATION: Glycine-NH2

<400> SEQUENCE: 20

Ile Phe Ser Leu Gly Gly Ser Pro Phe Pro Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Isoleucine
<221> NAME/KEY: MOD_RES
<222> LOCATION: (7)..(7)
<223> OTHER INFORMATION: Glutamine-NH2

<400> SEQUENCE: 21

Ile Phe Thr Tyr Gly Lys Gln
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Glycine
<221> NAME/KEY: MOD_RES
<222> LOCATION: (7)..(7)
<223> OTHER INFORMATION: Glycine-NH2

<400> SEQUENCE: 22

Gly Arg Val Pro Phe Pro Gly
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (7)..(7)
<223> OTHER INFORMATION: Glycine-NH2

<400> SEQUENCE: 23

Gly Arg Val Pro Phe Pro Gly
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (7)..(7)
<223> OTHER INFORMATION: Glycine-NH2

<400> SEQUENCE: 24
```

Gly Arg Met Pro Tyr Pro Gly
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (4)..(4)
<223> OTHER INFORMATION: D-Lysine
<221> NAME/KEY: MOD_RES
<222> LOCATION: (7)..(7)
<223> OTHER INFORMATION: Valine-NH2

<400> SEQUENCE: 25

Leu Val Thr Lys Gly Arg Val
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (7)..(7)
<223> OTHER INFORMATION: Valine-NH2

<400> SEQUENCE: 26

Leu Val Thr His Gly Arg Val
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Glycine
<221> NAME/KEY: MOD_RES
<222> LOCATION: (7)..(7)
<223> OTHER INFORMATION: Glutamine-NH2

<400> SEQUENCE: 27

Gly Lys Gln Pro Trp Tyr Gln
1               5

<210> SEQ ID NO 28
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Glycine
<221> NAME/KEY: MOD_RES
<222> LOCATION: (7)..(7)
<223> OTHER INFORMATION: Glycine-NH2

<400> SEQUENCE: 28

```
Gly Gly Ser Pro Tyr Pro Gly
1               5

<210> SEQ ID NO 29
<211> LENGTH: 6
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Valine
<221> NAME/KEY: MOD_RES
<222> LOCATION: (6)..(6)
<223> OTHER INFORMATION: Valine-NH2

<400> SEQUENCE: 29

Val Thr Lys Gly Arg Val
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Leucine
<221> NAME/KEY: MOD_RES
<222> LOCATION: (7)..(7)
<223> OTHER INFORMATION: Valine-NH2

<400> SEQUENCE: 30

Leu Thr Thr Lys Gly Arg Val
1               5

<210> SEQ ID NO 31
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (7)..(7)
<223> OTHER INFORMATION: Valine-NH2

<400> SEQUENCE: 31

Leu Thr Thr Lys Gly Arg Val
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (7)..(7)
<223> OTHER INFORMATION: Glycine-NH2

<400> SEQUENCE: 32

Gly Arg Val Pro Tyr Pro Gly
1               5

<210> SEQ ID NO 33
<211> LENGTH: 8
<212> TYPE: PRT
<213> ORGANISM: Artificial Sequence
<220> FEATURE:
```

```
<223> OTHER INFORMATION: synthetic
<221> NAME/KEY: MOD_RES
<222> LOCATION: (1)..(1)
<223> OTHER INFORMATION: (Diacetyl) Lysine
<221> NAME/KEY: MOD_RES
<222> LOCATION: (7)..(7)
<223> OTHER INFORMATION: Glycine-NH2

<400> SEQUENCE: 33

Lys Gly Arg Val Pro Tyr Pro Gly
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Isoleucine
<221> NAME/KEY: MOD_RES
<222> LOCATION: (7)..(7)
<223> OTHER INFORMATION: Isoleucine-NH2

<400> SEQUENCE: 34

Ile Val Thr His Gly Arg Ile
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Isoleucine
<221> NAME/KEY: MOD_RES
<222> LOCATION: (7)..(7)
<223> OTHER INFORMATION: Serine-NH2

<400> SEQUENCE: 35

Ile Ala Thr Tyr Gly Met Ser
1               5

<210> SEQ ID NO 36
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Isoleucine
<221> NAME/KEY: MOD_RES
<222> LOCATION: (7)..(7)
<223> OTHER INFORMATION: Valine-NH2

<400> SEQUENCE: 36

Ile Tyr Ser Phe Gly Arg Val
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
```

<223> OTHER INFORMATION: N-Acetyl-Leucine
<221> NAME/KEY: MOD_RES
<222> LOCATION: (7)..(7)
<223> OTHER INFORMATION: Proline-NH2

<400> SEQUENCE: 37

Leu Met Thr Arg Gly Ala Pro
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl-Glycine
<221> NAME/KEY: MOD_RES
<222> LOCATION: (2)..(2)
<223> OTHER INFORMATION: N-Nitroarginine
<221> NAME/KEY: MOD_RES
<222> LOCATION: (9)..(9)
<223> OTHER INFORMATION: Valine-NH2

<400> SEQUENCE: 38

Gly Arg Val Pro Tyr Pro Gly Met Val
1               5

<210> SEQ ID NO 39
<211> LENGTH: 11
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Glycine
<221> NAME/KEY: MOD_RES
<222> LOCATION: (11)..(11)
<223> OTHER INFORMATION: Lysine-NH2

<400> SEQUENCE: 39

Gly Arg Val Pro Tyr Pro Arg Ile Pro Leu Lys
1               5                   10

<210> SEQ ID NO 40
<211> LENGTH: 9
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Tyrosine
<221> NAME/KEY: MOD_RES
<222> LOCATION: (9)..(9)
<223> OTHER INFORMATION: Isoleucine-NH2

<400> SEQUENCE: 40

Tyr Gly Met Ser Pro Tyr Pro Gly Ile
1               5

<210> SEQ ID NO 41
<211> LENGTH: 11
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)

```
<223> OTHER INFORMATION: N-Acetyl Glycine
<221> NAME/KEY: MOD_RES
<222> LOCATION: (11)..(11)
<223> OTHER INFORMATION: Asparagine-NH2

<400> SEQUENCE: 41

Gly Val Lys Pro Phe Gln Gly Val Lys Asn Asn
1               5                  10

<210> SEQ ID NO 42
<211> LENGTH: 12
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Glutamic Acid
<221> NAME/KEY: MOD_RES
<222> LOCATION: (12)..(12)
<223> OTHER INFORMATION: Glycine-NH2

<400> SEQUENCE: 42

Glu Leu Val Thr Lys Gly Arg Val Pro Tyr Pro Gly
1               5                  10

<210> SEQ ID NO 43
<211> LENGTH: 12
<212> TYPE: PRT
<213> ORGANISM: Artificial Sequence
<220> FEATURE:
<223> OTHER INFORMATION: synthetic
<221> NAME/KEY: MOD_RES
<222> LOCATION: (12)..(12)
<223> OTHER INFORMATION: Glycine-NH2

<400> SEQUENCE: 43

Glu Leu Val Thr Lys Gly Arg Val Pro Tyr Pro Gly
1               5                  10

<210> SEQ ID NO 44
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Leucine
<221> NAME/KEY: MOD_RES
<222> LOCATION: (5)..(5)
<223> OTHER INFORMATION: D-Lysine
<221> NAME/KEY: MOD_RES
<222> LOCATION: (7)..(7)
<223> OTHER INFORMATION: Valine-NH2

<400> SEQUENCE: 44

Leu Val Thr Lys Lys Arg Val
1               5

<210> SEQ ID NO 45
<211> LENGTH: 7
<212> TYPE: PRT
<213> ORGANISM: Artificial Sequence
<220> FEATURE:
<223> OTHER INFORMATION: synthetic
<221> NAME/KEY: misc_feature
<222> LOCATION: (4)..(4)
<223> OTHER INFORMATION: Xaa is L-Lysine, D-Lysine, His, Tyr, Phe or Arg

<400> SEQUENCE: 45
```

```
Leu Val Thr Xaa Gly Arg Val
1               5

<210> SEQ ID NO 46
<211> LENGTH: 7
<212> TYPE: PRT
<213> ORGANISM: Artificial Sequence
<220> FEATURE:
<223> OTHER INFORMATION: synthetic
<221> NAME/KEY: misc_feature
<222> LOCATION: (5)..(5)
<223> OTHER INFORMATION: Xaa is Tyr, Phe or Trp
<221> NAME/KEY: misc_feature
<222> LOCATION: (7)..(7)
<223> OTHER INFORMATION: Xaa is Gly, Ala or Arg

<400> SEQUENCE: 46

Gly Arg Val Pro Xaa Pro Xaa
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Valine
<221> NAME/KEY: MOD_RES
<222> LOCATION: (7)..(7)
<223> OTHER INFORMATION: Valine-NH2

<400> SEQUENCE: 47

Val Val Thr Arg Gly Lys Val
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic
<221> NAME/KEY: MOD_RES
<222> LOCATION: (1)..(1)
<223> OTHER INFORMATION: N-Acetyl Glycine
<221> NAME/KEY: MOD_RES
<222> LOCATION: (7)..(7)
<223> OTHER INFORMATION: Benzylic ester of aspartic acid - NH2

<400> SEQUENCE: 48

Gly Ala Pro Pro Tyr Pro Asp
1               5

<210> SEQ ID NO 49
<211> LENGTH: 20
<212> TYPE: PRT
<213> ORGANISM: Artificial Sequence
<220> FEATURE:
<223> OTHER INFORMATION: synthetic
<221> NAME/KEY: misc_feature
<222> LOCATION: (1)..(1)
<223> OTHER INFORMATION: Xaa is Trp or Thr
<221> NAME/KEY: misc_feature
<222> LOCATION: (3)..(3)
<223> OTHER INFORMATION: Xaa is Ile or Leu
<221> NAME/KEY: misc_feature
<222> LOCATION: (4)..(4)
<223> OTHER INFORMATION: Xaa is any amino acid
<221> NAME/KEY: misc_feature
<222> LOCATION: (5)..(5)
```

```
<223> OTHER INFORMATION: Xaa is Thr or Ser
<221> NAME/KEY: misc_feature
<222> LOCATION: (6)..(6)
<223> OTHER INFORMATION: Xaa is any amino acid
<221> NAME/KEY: misc_feature
<222> LOCATION: (8)..(9)
<223> OTHER INFORMATION: Xaa is any amino acid
<221> NAME/KEY: misc_feature
<222> LOCATION: (11)..(11)
<223> OTHER INFORMATION: Xaa is Tyr of Phe
<221> NAME/KEY: misc_feature
<222> LOCATION: (14)..(14)
<223> OTHER INFORMATION: Xaa is Val, Thr or Met
<221> NAME/KEY: misc_feature
<222> LOCATION: (15)..(17)
<223> OTHER INFORMATION: Xaa is any amino acid
<221> NAME/KEY: misc_feature
<222> LOCATION: (18)..(18)
<223> OTHER INFORMATION: Xaa is Glu or Asp
<221> NAME/KEY: misc_feature
<222> LOCATION: (19)..(19)
<223> OTHER INFORMATION: Xaa is Val, Ile or Ala
<221> NAME/KEY: misc_feature
<222> LOCATION: (20)..(20)
<223> OTHER INFORMATION: Xaa is Leu, Met, Val or Ile

<400> SEQUENCE: 49

Xaa Glu Xaa Xaa Xaa Xaa Gly Xaa Xaa Pro Xaa Pro Gly Xaa Xaa Xaa
1               5                   10                  15

Xaa Xaa Xaa Xaa
            20

<210> SEQ ID NO 50
<211> LENGTH: 20
<212> TYPE: PRT
<213> ORGANISM: Artificial Sequence
<220> FEATURE:
<223> OTHER INFORMATION: synthetic
<221> NAME/KEY: misc_feature
<222> LOCATION: (2)..(2)
<223> OTHER INFORMATION: Xaa is Glu, Asp, or a substituted or
      unsubstituted aliphatic, benzylic or aromatic ester of aspartic
      acid or of glutamic acid
<221> NAME/KEY: misc_feature
<222> LOCATION: (3)..(3)
<223> OTHER INFORMATION: Xaa is Ile, Val, Met or Leu
<221> NAME/KEY: misc_feature
<222> LOCATION: (4)..(4)
<223> OTHER INFORMATION: Xaa is Val, Ile, Met or Leu
<221> NAME/KEY: misc_feature
<222> LOCATION: (5)..(5)
<223> OTHER INFORMATION: Xaa is Thr or Ser
<221> NAME/KEY: misc_feature
<222> LOCATION: (6)..(6)
<223> OTHER INFORMATION: Xaa is Leu, Val, Met or Ile
<221> NAME/KEY: misc_feature
<222> LOCATION: (7)..(8)
<223> OTHER INFORMATION: Xaa is Gly or Ala
<221> NAME/KEY: misc_feature
<222> LOCATION: (9)..(9)
<223> OTHER INFORMATION: Xaa is Asn or Gln
<221> NAME/KEY: misc_feature
<222> LOCATION: (11)..(11)
<223> OTHER INFORMATION: Xaa is Tyr, Trp or Phe
<221> NAME/KEY: misc_feature
<222> LOCATION: (13)..(13)
<223> OTHER INFORMATION: Xaa is Gly or Ala
<221> NAME/KEY: misc_feature
<222> LOCATION: (14)..(14)
<223> OTHER INFORMATION: Xaa is Ile, Val, Met or Leu
<221> NAME/KEY: misc_feature
<222> LOCATION: (17)..(17)
<223> OTHER INFORMATION: Xaa is Glu, Asp, or a substituted or
      unsubstituted aliphatic, benzylic or aromatic ester of aspartic
      acid or of glutamic acid
<221> NAME/KEY: misc_feature
```

```
<222> LOCATION: (18)..(18)
<223> OTHER INFORMATION: Xaa is Arg; N-nitroarginine,
      beta-cycloarginine, gamma-hyddroxyarginine, amidinocitroline or
      2-amino-4-guanidinobutanoic acid; Lys; or Ornithine
<221> NAME/KEY: misc_feature
<222> LOCATION: (19)..(19)
<223> OTHER INFORMATION: Xaa is Leu, Met, Val or Ile
<221> NAME/KEY: misc_feature
<222> LOCATION: (20)..(20)
<223> OTHER INFORMATION: Xaa is Phe, Trp or Tyr

<400> SEQUENCE: 50

Trp Xaa Xaa Xaa Xaa Xaa Xaa Xaa Xaa Pro Xaa Pro Xaa Xaa Pro Pro
1               5                   10                  15

Xaa Xaa Xaa Xaa
            20

<210> SEQ ID NO 51
<211> LENGTH: 12
<212> TYPE: PRT
<213> ORGANISM: Artificial Sequence
<220> FEATURE:
<223> OTHER INFORMATION: synthetic
<221> NAME/KEY: misc_feature
<222> LOCATION: (4)..(4)
<223> OTHER INFORMATION: Xaa is Ser or Thr
<221> NAME/KEY: misc_feature
<222> LOCATION: (8)..(8)
<223> OTHER INFORMATION: Xaa is Ser or Thr

<400> SEQUENCE: 51

Glu Ile Phe Xaa Leu Gly Gly Xaa Pro Tyr Pro Gly
1               5                   10

<210> SEQ ID NO 52
<211> LENGTH: 12
<212> TYPE: PRT
<213> ORGANISM: Artificial Sequence
<220> FEATURE:
<223> OTHER INFORMATION: synthetic

<400> SEQUENCE: 52

Glu Ile Phe Thr Tyr Gly Lys Gln Pro Trp Tyr Gln
1               5                   10

<210> SEQ ID NO 53
<211> LENGTH: 12
<212> TYPE: PRT
<213> ORGANISM: Artificial Sequence
<220> FEATURE:
<223> OTHER INFORMATION: synthetic

<400> SEQUENCE: 53

Glu Leu Val Thr Lys Gly Arg Val Pro Tyr Pro Gly
1               5                   10
```